(12) United States Patent
Suzuki et al.

(10) Patent No.: US 9,408,800 B2
(45) Date of Patent: Aug. 9, 2016

(54) COSMETIC COMPOSITION

(71) Applicant: KAO CORPORATION, Chuo-ku (JP)

(72) Inventors: Hirohisa Suzuki, Funabashi (JP);
Yoshiaki Matsui, Izumisano (JP);
Takashi Kodate, Wakayama (JP)

(73) Assignee: KAO CORPORATION, Chuo-ku (JP)

( * ) Notice: Subject to any disclaimer, the term of this patent is extended or adjusted under 35 U.S.C. 154(b) by 0 days.

(21) Appl. No.: 14/380,608

(22) PCT Filed: Feb. 25, 2013

(86) PCT No.: PCT/JP2013/054799
§ 371 (c)(1),
(2) Date: Aug. 22, 2014

(87) PCT Pub. No.: WO2013/129330
PCT Pub. Date: Sep. 6, 2013

(65) Prior Publication Data
US 2015/0037418 A1 Feb. 5, 2015

(30) Foreign Application Priority Data

Feb. 28, 2012 (JP) ................. 2012-041704

(51) Int. Cl.
| | |
|---|---|
| *A61K 8/898* | (2006.01) |
| *A61K 8/58* | (2006.01) |
| *A61K 8/06* | (2006.01) |
| *A61K 8/02* | (2006.01) |
| *A61K 8/27* | (2006.01) |
| *A61K 8/897* | (2006.01) |
| *A61Q 1/02* | (2006.01) |
| *A61Q 1/00* | (2006.01) |
| *A61Q 1/12* | (2006.01) |
| *A61Q 17/04* | (2006.01) |
| *A61Q 1/08* | (2006.01) |
| *A61Q 1/10* | (2006.01) |
| *A61Q 1/04* | (2006.01) |

(52) U.S. Cl.
CPC ............... *A61K 8/898* (2013.01); *A61K 8/022* (2013.01); *A61K 8/0241* (2013.01); *A61K 8/064* (2013.01); *A61K 8/27* (2013.01); *A61K 8/585* (2013.01); *A61K 8/897* (2013.01); *A61Q 1/00* (2013.01); *A61Q 1/02* (2013.01); *A61Q 1/12* (2013.01); *A61Q 17/04* (2013.01); *A61K 2800/5922* (2013.01); *A61K 2800/612* (2013.01); *A61K 2800/87* (2013.01); *A61Q 1/04* (2013.01); *A61Q 1/08* (2013.01); *A61Q 1/10* (2013.01)

(58) Field of Classification Search
None
See application file for complete search history.

(56) References Cited

U.S. PATENT DOCUMENTS

| | | | |
|---|---|---|---|
| 5,548,054 | A | 8/1996 | Okada et al. |
| 5,700,898 | A | 12/1997 | Okada et al. |

(Continued)

FOREIGN PATENT DOCUMENTS

| | | |
|---|---|---|
| EP | 0 640 644 A1 | 1/1995 |
| EP | 2 233 126 A1 | 9/2010 |

(Continued)

OTHER PUBLICATIONS

International Preliminary Report on Patentability and Written Opinion issued Sep. 12, 2014, in International Application No. PCT/JP2013/054799.

(Continued)

*Primary Examiner* — Robert A Wax
*Assistant Examiner* — Caralynne Helm
(74) *Attorney, Agent, or Firm* — Oblon, McClelland, Maier & Neustadt, L.L.P

(57) ABSTRACT

A cosmetic composition, comprising the following components (A), (B), (C), and (D):
(A) from 0.01 to 50% by mass of a fluorine-modified silicone having a polysiloxane unit represented by the following formulae (1) and (2):
wherein, Rf represents a perfluoroalkyl group having 6 carbon atoms; $R^1$, $R^2$, and $R^3$ each represent a hydrocarbon group having 1 to 6 carbon atoms; m represents a number of from 2 to 6; n represents a number of from 1 to 6; p represents a number of from 3 to 50; s represents a number of from 1 to 5; and a ratio between p and s satisfies $0.66 \leq p/(p+s) \leq 0.9$,
(B) from 0.01 to 40% by mass of a powder having been subjected to a surface treatment with tridecafluoro octyl-triethoxysilane,
(C) from 0.01 to 20% by mass of a fine zinc oxide particle having a specific surface area of from 10 to 100 m²/g, with the proviso that the component (B) is excluded from the component (C), and
(D) from 0.01 to 10% by mass of a specific poly(N-acylalkyleneimine)-modified organopolysiloxane,
and wherein, a mass ratio of the component (A) to the component (D), (A)/(D), is from 0.1 to 100.

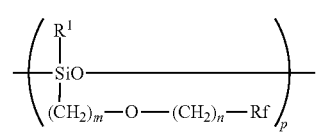

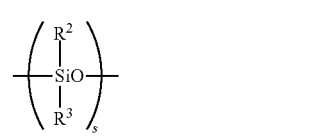

21 Claims, No Drawings

(56) References Cited

U.S. PATENT DOCUMENTS

| | | | |
|---|---|---|---|
| 5,976,518 A | 11/1999 | Okada et al. | |
| 6,018,082 A | 1/2000 | Okada et al. | |
| 2003/0228339 A1* | 12/2003 | El-Nokaly | A61K 8/0241 424/401 |
| 2010/0269733 A1* | 10/2010 | Kremitzl | B82Y 30/00 106/404 |
| 2011/0110995 A1 | 5/2011 | Hasegawa et al. | |

FOREIGN PATENT DOCUMENTS

| | | |
|---|---|---|
| JP | 02-295913 A | 12/1990 |
| JP | 06-184312 A | 7/1994 |
| JP | 07-277914 A | 10/1995 |
| JP | 07-330544 A | 12/1995 |
| JP | 08-026931 A | 1/1996 |
| JP | 08-040831 A | 2/1996 |
| JP | 09-249518 A | 9/1997 |
| JP | 10-139623 A | 5/1998 |
| JP | 2008-143821 A | 6/2008 |
| JP | 2008-143837 A | 6/2008 |
| JP | 2009-035511 A | 2/2009 |
| JP | 2011-16732 A | 1/2011 |
| TW | 201032832 A1 | 9/2010 |

OTHER PUBLICATIONS

International Search Report issued May 28, 2013 in PCT/JP2013/054799 filed Feb. 25, 2013.

Extended European Search Report issued Oct. 9, 2015 in Patent Application No. 13755284.0.

* cited by examiner

COSMETIC COMPOSITION

CROSS REFERENCE TO RELATED APPLICATION

This application is a 371 of PCT/JP2013/054799, filed on Feb. 25, 2013, and claims priority to Japanese Patent Application No. 2012-041704, filed on Feb. 28, 2012.

FIELD OF THE INVENTION

The present invention relates to a cosmetic composition.

BACKGROUND OF THE INVENTION

When only conventional powders are incorporated into cosmetic compositions, the powders are markedly wetted with sweat, sebum, and the like on the skin, eventually presenting a mirror-like appearance. This makes it difficult to maintain the makeup finish immediately after application. In light of this, with the aim of improving durability of makeup and preventing makeup deterioration, cosmetic compositions containing various water and oil repellent compounds have been studied.

For example, Patent Literature 1 describes a cosmetic composition containing a specific fluorine-modified silicone derivative and Patent Literature 2 describes a cosmetic composition containing a fluorine-modified silicone and a fine zinc oxide particle.

It has been proposed that these cosmetic compositions strongly prevent makeup deterioration and have excellent durability of makeup.

CITATION LIST

Patent Literature

[Patent Literature 1] JP-A-6-184312
[Patent Literature 2] JP-A-7-277914

SUMMARY OF THE INVENTION

The present invention relates to a cosmetic composition, comprising the following components (A), (B), (C), and (D):
(A) from 0.01 to 50% by mass of a fluorine-modified silicone having a polysiloxane unit represented by the following formulae (1) and (2):

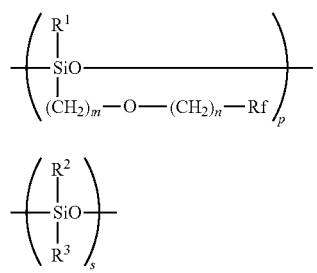

wherein, Rf represents a linear or branched perfluoroalkyl group having 6 carbon atoms; $R^1$, $R^2$, and $R^3$ are the same or different and each represent a linear or branched hydrocarbon group having 1 to 6 carbon atoms; m represents a number of from 2 to 6; n represents a number of from 1 to 6; p represents a number of from 3 to 50; s represents a number of from 1 to 5; and a ratio between p and s satisfies $0.66 \leq p/(p+s) \leq 0.9$, (B) from 0.01 to 40% by mass of a powder having been subjected to a surface treatment with tridecafluoro octyltriethoxysilane, (C) from 0.01 to 20% by mass of a fine zinc oxide particle having a specific surface area of from 10 to 100 m²/g, with the proviso that the component (B) is excluded from the component (C), and (D) from 0.01 to 10% by mass of an organopolysiloxane in which poly(N-acylalkyleneimine) segments are bound to at least two silicon atoms of an organopolysiloxane segment constituting a main chain via alkylene groups each having a hetero atom, the poly(N-acylalkyleneimine) segments comprising a repeating unit represented by the following formula (4):

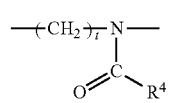

wherein, $R^4$ represents a hydrogen atom or an alkyl group having 1 to 3 carbon atoms and t represents 2 or 3, wherein, a number average molecular weight of the poly(N-acylalkyleneimine) segment is from 500 to 4000, a mass ratio of (a) the organopolysiloxane segment constituting the main chain to (b) the poly(N-acylalkyleneimine) segment, (a/b), is from 80/20 to 95/5, a weight average molecular weight of the organopolysiloxane segment between adjacent poly(N-acylalkyleneimine) segments is from 10000 to 40000, and a weight average molecular weight of the organopolysiloxane segment constituting the main chain is from 50000 to 150000, and wherein, a mass ratio of the component (A) to the component (D), (A)/(D), is from 0.1 to 100.

DETAILED DESCRIPTION OF THE INVENTION

The present inventors have found a problem that, after application to the skin, the effect of covering uneven skin tone such as blemishes and freckles is impaired, the skin becomes dull, the pores stand out, and the skin texture appears rough. They have also found another problem that due to the low surface free energy of fluorine compounds, cosmetic compositions have poor adhesion and attachment to the skin.

The present invention relates to a cosmetic composition which can improve the dullness of the skin, make pores less noticeable, and fix the skin texture, and which has good adhesion and attachment to the skin.

The present inventors have found that a cosmetic which solves the aforementioned problems can be obtained by using a combination of a specific fluorine-modified silicone, a powder treated with a fluorine compound, a fine zinc oxide particle, and a specific poly(N-acylalkyleneimine)-modified organopolysiloxane.

The cosmetic composition of the present invention, which can realize a flawless makeup finish, make pores less noticeable, and fix the skin texture, and which has excellent adhesion and attachment to the skin, can be obtained.

The fluorine-modified silicone of the component (A) used in the present invention has a polysiloxane unit represented by the above formulae (1) and (2).

In the formulae, examples of the hydrocarbon groups represented by $R^1$, $R^2$, and $R^3$ include a linear alkyl group such as a methyl group, an ethyl group, a propyl group, a butyl group, a pentyl group, and a hexyl group; a branched alkyl group such as an isopropyl group, a sec-butyl group, a tert-butyl group, a neopentyl group, and a 1-ethylpropyl group; and a cyclic alkyl group such as cyclopentyl and cyclohexyl.

Also, m represents a number of from 2 to 6, preferably from 2 to 5, more preferably 3. Also, n represents a number of from 1 to 6, preferably from 1 to 4, more preferably 2.

Also, p represents a number of from 3 to 50, preferably from 3 to 10, more preferably from 3 to 6. Also, s represents a number of from 1 to 5, preferably from 1 to 3, more preferably 1.

Also, in order to successfully improve the dullness of the skin, make pores less noticeable, and fix the skin texture with excellent covering effects and achieve adhesion to the skin, the ratio between p and s, namely, the modification rate of the polysiloxane unit p represented by the formula (1) to the sum of the polysiloxane units p+s represented by the formulae (1) and (2), satisfies $0.66 \leq p/(p+s) \leq 0.9$, preferably $0.75 \leq p/(p+s) \leq 0.83$.

The fluorine-modified silicone of the component (A) can be produced in accordance with, for example, the method described in JP-A-6-184312.

As the component (A), a fluorine-modified silicone represented by the following formula (3) is preferable.

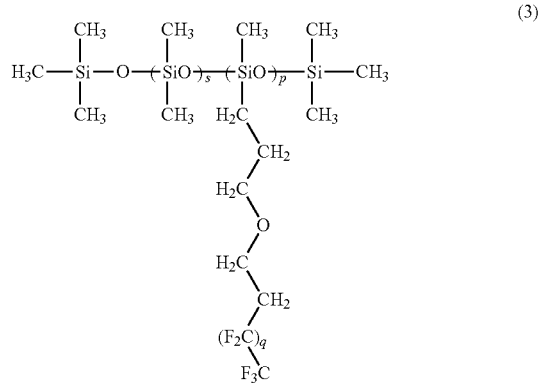

wherein, p and s have the same meaning as above and q represent a number of 5.

The component (A) can be used singly or in combination of two or more thereof, and in order to improve the dullness of the skin, make pores less noticeable, and fix the skin texture, the content thereof is, relative to the whole cosmetic composition, 0.01% by mass or more, preferably 0.1% by mass or more, more preferably 1% by mass or more, even more preferably 4% by mass or more, and 50% by mass or less, preferably 30% by mass or less, more preferably 20% by mass or less, even more preferably 15% by mass or less. Further, the content of the component (A) is from 0.01 to 50% by mass, preferably from 0.1 to 30% by mass, more preferably from 1 to 20% by mass, and even more preferably from 4 to 15% by mass of the total composition.

The powder of the component (B) used in the present invention is a powder having been subjected to a surface treatment with tridecafluoro octyltriethoxysilane represented by the following formula.

$$F_3C-(CF_2)_5-(CH_2)_2-Si-(OCH_2CH_3)_3$$

A powder having been subjected to a surface treatment with tridecafluoro octyltriethoxysilane of fluorine compounds used for the surface treatment of the powder can be used in combination with the component (A) to improve the dullness of the skin, create a makeup finish with bright skin, make pores less noticeable, and fix the skin texture. As tridecafluoro octyltriethoxysilane, FHS sold by Daito Kasei Kogyo Co., Ltd. is preferable.

The powder to be treated is not particularly limited as long as it is an extender pigment or color pigment used in conventional cosmetics. Examples thereof include an inorganic powder such as silicic acid, silicic acid anhydride, magnesium silicate, talc, sericite, mica, kaolin, red iron oxide, clay, bentonite, titanium-coated mica, bismuth oxychloride, zirconium oxide, magnesium oxide, titanium oxide, zinc oxide, aluminum oxide, calcium sulfate, barium sulfate, magnesium sulfate, calcium carbonate, magnesium carbonate, iron oxide, ultramarine, chromium oxide, chromium hydroxide, calamine, and carbon black, and a complex of these materials; an organic powder such as polyamide, polyester, polypropylene, polystyrene, polyurethane, vinyl resin, urea resin, phenolic resin, fluororesin, silicone resin, acrylic resin, melamine resin, epoxy resin, polycarbonate resin, a divinylbenzene-styrene copolymer, silk powder, cellulose, long-chain alkyl phosphate metal salt, N-mono long-chain alkyl acyl basic amino acid, and a complex of these materials; and further, a complex powder of the aforementioned inorganic powder and organic powder. Among these materials, titanium oxide, red iron oxide, yellow iron oxide, black iron oxide, mica, titanium-coated mica, nylon powder, silica, talc, and sericite are preferable.

As a method of surface treatment of a powder with tridecafluoro octyltriethoxysilane, for example, the following methods can be performed, which are: a method comprising dropping or adding tridecafluoro octyltriethoxysilane to a powder and mixing them in a mixer, followed by heat treatment and, if necessary, crushing; and a method comprising dissolving or dispersing tridecafluoro octyltriethoxysilane in an organic solvent, and then mixing the resulting organic solvent solution with a powder, followed by removing the organic solvent, and then crushing the product obtained after drying.

Among those methods, the following method is given as a preferred method: a production method comprising dissolving or dispersing tridecafluoro octyltriethoxysilane in an organic solvent and, while mixing the resulting organic solvent with a powder in a mixer, removing the organic solvent by heating the mixer under reduced pressure, followed by heat treatment and crushing as needed. Suitable examples of the organic solvent used in this method include a polar organic solvent represented by methanol, ethanol, isopropyl alcohol, isobutanol, acetone, ethyl acetate, butyl acetate, methyl ethyl ketone, dichloromethane, and chloroform and a hydrocarbon organic solvent such as normal hexane, toluene, and xylene.

The amount of tridecafluoro octyltriethoxysilane used in the treatment varies depending on the powder; however, the amount of tridecafluoro octyltriethoxysilane used in the treatment is preferably 0.05% by mass or more, more preferably 0.1% by mass or more, preferably 50% by mass or less, more preferably 20% by mass or less. Also, relative to the mass of the powder of the component (B), the amount of tridecafluoro octyltriethoxysilane used in the treatment is preferably from 0.05 to 50% by mass, more preferably from 0.1 to 20% by mass. It is preferable that the amount of tridecafluoro octyltriethoxysilane used in the treatment be in the above range so that the resulting cosmetic exerts sufficient water and oil repellent properties and achieves favorable feeling to the touch and fluidity.

In consideration of powderiness during application and makeup finish, the average particle diameter of the component (B) is preferably from 0.1 to 20 μm, more preferably from 0.1 to 10 μm.

It should be noted that in the present invention, the particle diameter of the component (B) is measured by electron microscopic observation or by the laser diffraction/scattering method using a particle size distribution measuring device. Specifically, in the case of the laser diffraction/scattering method, the particle diameter of the component (B) is measured by a laser diffraction scattering particle size distribution measuring device (for example, Model LA-920, the product of Horiba, Ltd.), using ethanol as a dispersion medium.

The component (B) can be used singly or in combination of two or more thereof, and in consideration of makeup finish and stability, the content thereof is, relative to the whole cosmetic composition, 0.01% by mass or more, preferably 0.1% by mass or more, more preferably 1% by mass or more, even more preferably 5% by mass or more, and 40% by mass or less, preferably 30% by mass or less, more preferably 25% by mass or less, and even more preferably 20% by mass or less. Also, the content of the component (B) is from 0.01 to 40% by mass, preferably from 0.1 to 30% by mass, more preferably from 1 to 25% by mass, and even more preferably from 5 to 20% by mass of the total composition.

In consideration of the feeling upon application and durability of makeup, in the present invention, the mass ratio of component (A) to component (B), (A)/(B), is preferably 0.01 or more, more preferably 0.1 or more, even more preferably 0.2 or more, and preferably 50 or less, more preferably 20 or less, even more preferably 10 or less, and further preferably 2 or less. Also, the mass ratio of component (A) to component (B), (A)/(B), is preferably from 0.01 to 50, more preferably from 0.1 to 20, even more preferably from 0.1 to 10, and further preferably from 0.2 to 2.

The fine zinc oxide particle of the component (C) used in the present invention is a fine zinc oxide particle having a specific surface area of from 10 to 100 m²/g, preferably from 15 to 95 m²/g. A fine zinc oxide particle having such a specific surface area can be used to provide excellent durability of makeup, make pores less noticeable, improve the dullness of the skin, create a makeup finish with bright skin, and provide favorable feeling upon application.

It should be noted that the component (C) used in the present invention excludes the component (B), meaning that the component (C) does not include the component (B).

Although the fine zinc oxide particle of the component (C) can be directly used, it is also possible to use a fine zinc oxide particle which has been subjected to a water and/or an oil repellent treatment with silicone, metal soap, lecithin, N-acylamino acid, a fluorine compound, and the like, as needed. In order to prevent makeup deterioration and improve the dispersibility of fine zinc oxide particles in the cosmetic composition, a silicone-treated fine zinc oxide particle is preferable, and it is more preferable to perform a silicone treatment using methyl hydrogen polysiloxane. These treatments can be performed in accordance with conventional methods.

The component (C) can be used singly or in combination of two or more thereof, and in order to make pores less noticeable, improve the dullness of the skin, and create a makeup finish with bright skin, the content thereof is, relative to the whole cosmetic composition, 0.01% by mass or more, preferably 0.1% by mass or more, more preferably 1% by mass or more, and 20% by mass or less, preferably 15% by mass or less, and more preferably 10% by mass or less. Also, the content of the component (C) is from 0.01 to 20% by mass, preferably from 0.1 to 15% by mass, and more preferably from 1 to 10% by mass of the total composition.

In order to improve the sustainability of makeup and the dullness of the skin, and create a makeup finish with bright skin, in the present invention, the mass ratio of the component (A) to the component (C), (A)/(C), is preferably 0.1 or more, more preferably 1 or more, and preferably 10 or less, more preferably 7 or less. Also, the mass ratio of the component (A) to the component (C), (A)/(C), is preferably from 0.1 to 10, more preferably from 1 to 7.

The component (D) is an organopolysiloxane in which poly(N-acylalkyleneimine) segments are bound to at least two silicon atoms of an organopolysiloxane segment constituting the main chain via alkylene groups each having a hetero atom, the poly(N-acylalkyleneimine) segments comprising a repeating unit represented by the following formula (4):

wherein, $R^4$ represents a hydrogen atom or an alkyl group having 1 to 3 carbon atoms and t represents 2 or 3, wherein, the number average molecular weight of the poly(N-acylalkyleneimine) segment is from 500 to 4000;

the mass ratio of (a) the organopolysiloxane segment constituting the main chain to (b) the poly(N-acylalkyleneimine) segment, (a/b), is from 80/20 to 95/5; the weight average molecular weight of the organopolysiloxane segment between adjacent poly(N-acylalkyleneimine) segments is from 10000 to 40000; and the weight average molecular weight of the organopolysiloxane segment constituting the main chain is from 50000 to 150000. By using the component (D), higher stability can be achieved.

At least two poly(N-acylalkyleneimine) segments are bound to an arbitrary silicon atom constituting the aforementioned organopolysiloxane segment via an alkylene group having a hetero atom. Further, it is preferable that poly(N-acylalkyleneimine) segments be bound to one or more silicon atoms other than those at both ends of the aforementioned organopolysiloxane segment via the aforementioned alkylene group(s), and it is more preferable that poly(N-acylalkyleneimine) segments be bound to two or more silicon atoms other than those at both ends via the aforementioned alkylene groups. That is, the organopolysiloxane of the component (D) is a graft polymer containing, as a side chain, at least two or more poly(N-acylalkyleneimine) segments comprising a repeating unit represented by the above formula (4).

The alkylene group having a hetero atom functions as a linking group of the poly(N-acylalkyleneimine) segment. Examples of the alkylene group include an alkylene group having 2 to 20 carbon atoms, which contains 1 to 3 nitrogen atoms, oxygen atoms, or sulfur atoms. Among them, a group represented by any one of the following formulae (i) to (vii) is preferable, and a group represented by the following formula (i) or (ii) is more preferable, and a group represented by the following formula (i) is even more preferable. It should be noted that, in the formulae, An⁻ represents a counterion of a quaternary ammonium salt, and examples thereof include an ethyl sulfate ion, a methyl sulfate ion, a chloride ion, an iodide ion, a sulfate ion, a p-toluene sulfonate ion, and a perchlorate ion.

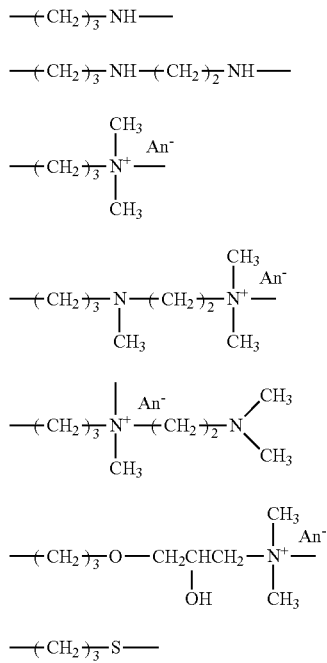

In the N-acylalkyleneimine unit constituting the poly(N-acylalkyleneimine) segment, examples of the alkyl group having 1 to 3 carbon atoms as $R^4$ in the formula (4) include a linear alkyl group having 1 to 3 carbon atoms or a branched alkyl group having 3 carbon atoms. Specific examples thereof include a methyl group, an ethyl group, a n-propyl group, and an isopropyl group.

In the formula (4), t represents a number of 2 or 3, and from the viewpoint of acquisition of the raw materials for the production of organopolysiloxane, t is preferably 2.

The mass ratio (a/b) is in the range of from 80/20 to 95/5, preferably from 83/17 to 93/7, more preferably from 85/15 to 90/10 so that the resulting cosmetic composition is excellent in attachment to the skin and emulsifiability, and improves the dullness of the skin, allowing the skin to look brighter.

Also, in the present specification, the mass ratio (a/b) refers to a value obtained from the integration ratio of the alkyl group or the phenyl group in the organopolysiloxane segment to the methylene group in the poly(N-acylalkyleneimine) segment as measured by nuclear magnetic resonance ($^1$H-NMR) analysis using deuterated chloroform in which 5% by mass of the organopolysiloxane of the component (D) is dissolved.

In the organopolysiloxane of the component (D), the weight average molecular weight (hereinbelow, sometimes also be simply referred to as "MWg") of the organopolysiloxane segment between adjacent poly(N-acylalkyleneimine) segments is in the range of from 10000 to 40000, and in consideration of the film flexibility and oil-water interfacial orientation, the above weight average molecular weight is more preferably from 15000 to 35000, even more preferably from 18000 to 32000.

According to the present invention, the "organopolysiloxane segment between adjacent poly(N-acylalkyleneimine) segments" indicates a segment surrounded by a broken line in the following formula (5), which is a segment between a linkage point of the poly(N-acylalkyleneimine) segment to the organopolysiloxane segment (shown as linkage point A) and a linkage point of the adjacent poly(N-acylalkyleneimine) segment (shown as linkage point B), comprising one $R^5SiO$ unit, one $R^6$, and the (y+1) number of $(R^5)_2SiO$ unit. Also, the "poly(N-acylalkyleneimine) segment" refers to the —Z—$R^7$ moiety connected to the aforementioned $R^6$.

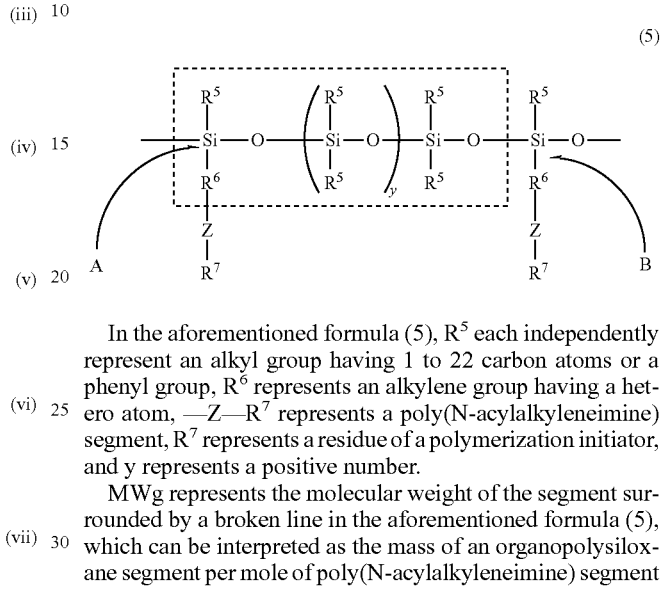

In the aforementioned formula (5), $R^5$ each independently represent an alkyl group having 1 to 22 carbon atoms or a phenyl group, $R^6$ represents an alkylene group having a hetero atom, —Z—$R^7$ represents a poly(N-acylalkyleneimine) segment, $R^7$ represents a residue of a polymerization initiator, and y represents a positive number.

MWg represents the molecular weight of the segment surrounded by a broken line in the aforementioned formula (5), which can be interpreted as the mass of an organopolysiloxane segment per mole of poly(N-acylalkyleneimine) segment (g/mol). It is to be noted that when 100% of the functional groups of the modified organopolysiloxane, which serves as the raw material compound, are substituted with poly(N-acylalkyleneimine), MWg equals to the functional group equivalent (g/mol) of modified organopolysiloxane.

The molecular weight of the poly(N-acylalkyleneimine) segment can be calculated from the molecular weight and the degree of polymerization of N-acylalkyleneimine unit, or measured by gel permeation chromatography (hereinbelow, sometimes also be simply referred to as "GPC") method. It is to be noted that, according to the present invention, the molecular weight of the poly(N-acylalkyleneimine) segment refers to the number average molecular weight in terms of polystyrene (hereinbelow, sometimes also be simply referred to as "MNox") as measured by GPC measurement performed under the measurement conditions to be described later. When MNox is in the range of from 500 to 4000, the film flexibility and solubility in a solvent can be improved. From this viewpoint, the aforementioned MNox is preferably from 800 to 3500, more preferably from 1000 to 3000.

Also, the aforementioned MWg can be obtained based on the content ratio (% by mass) of the organopolysiloxane segment constituting the main chain (hereinbelow, sometimes also be simply referred to as "Csi") by the following formula (I).

$$MWg = Csi \times MNox/(100-Csi) \qquad (I)$$

The weight average molecular weight of the organopolysiloxane segment constituting the main chain (hereinbelow, sometimes also be simply referred to as "MWsi") is from 50000 to 150000, and in consideration of flexibility and attachment to the skin, the weight average molecular weight of the organopolysiloxane segment constituting the main chain is preferably from 70000 to 130000, more preferably from 90000 to 110000. Also, the organopolysiloxane of the component (D) can be easily incorporated into various products by dissolving it in a polar solvent such as water. Because the organopolysiloxane segment constituting the main chain shares a common skeleton with the modified organopolysiloxane which serves as the raw material compound, MWsi is roughly equal to the weight average molecular weight of the modified organopolysiloxane, which serves as the raw material compound. It should be noted that the weight average molecular weight of the modified organopolysiloxane, which serves as the raw material compound, is measured by GPC under the measurement conditions to be described later and expressed in terms of polystyrene.

From the viewpoint of achieving both attachment to the skin and emulsion stability, the weight average molecular weight of the organopolysiloxane of the component (D) (hereinbelow, sometimes also be simply referred to as "MWt") is preferably from 60000 to 160000, more preferably from 80000 to 140000, and even more preferably from 100000 to 120000. The MWt value is measured by GPC under the measurement conditions to be described later and expressed in terms of polystyrene.

The organopolysiloxane of the component (D) has, in addition to a high elastic modulus and a large deformation amount, such unique thermoplasticity that when it is heated to a temperature range of 50 to 220° C., it becomes soft with markedly improved plasticity, but when the temperature drops to room temperature after heating is stopped, it immediately restores its elasticity.

The organopolysiloxane of the component (D) is produced by, for example, reacting a modified organopolysiloxane with a terminal reactive poly(N-acylalkyleneimine), the modified organopolysiloxane being represented by the following formula (6):

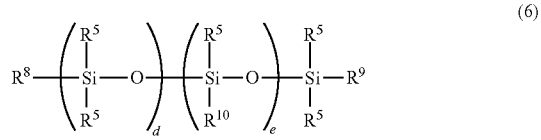

wherein, $R^5$ has the same meaning as above; and $R^8$ and $R^9$ each represent the same group as $R^5$ or a monovalent group represented by any of the following formulae (viii) to (xiii):

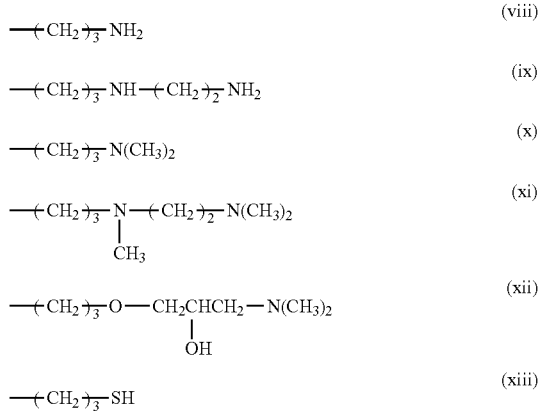

$R^{10}$ represents a monovalent group represented by the above formulae (viii) to (xiii); d represents a number of from 91.5 to 1255.0; and e represents a number of from 2.0 to 62.5; and the terminal reactive poly(N-acylalkyleneimine) being obtainable by ring-opening polymerization of a cyclic imino ether represented by the following formula (7):

wherein, $R^4$ and t have the same meaning as above.

For the ring-opening polymerization of the cyclic imino ether represented by the formula (7) (hereinbelow, sometimes also be simply referred to as "cyclic imino ether (7)"), a polymerization initiator can be used. As the polymerization initiator, a compound having high electrophilic reactivity, for example, an alkyl ester of a strong acid such as alkylbenzene sulfonate, alkyl p-toluenesulfonate, alkyl trifluoromethanesulfonate, alkyl trifluoroacetate, and dialkyl sulfate, can be used. Among them, dialkyl sulfate is preferably used.

Examples of a solvent for polymerization include acetic acid esters such as ethyl acetate and propyl acetate, ethers such as diethyl ether, diisopropyl ether, dioxane, and tetrahydrofuran, ketones such as acetone and methyl ethyl ketone, a halogen solvent such as chloroform and methylene chloride, a nitrile solvent such as acetonitrile and benzonitrile, and an aprotic polar solvent such as N,N-dimethylformamide, N,N-dimethylacetamide, and dimethylsulfoxide. Among them, acetic acid esters are preferably used. The amount of the solvent used is normally 20 to 2,000 parts by mass relative to 100 parts by mass of the cyclic imino ether (7).

The polymerization temperature is normally 30 to 170° C., preferably 40 to 150° C. Although the polymerization time varies depending on factors such as polymerization temperature, it is normally 1 to 60 hours.

For example, when 2-substituted-2-oxazoline is used as the cyclic imino ether (7), poly(N-acylethyleneimine) with t=2 in the above formula (4) can be obtained, while when 2-substituted-dihydro-2-oxazine is used, poly(N-acylpropyleneimine) with t=3 in the above formula (4) can be obtained.

Poly(N-acylalkyleneimine) obtainable by the living polymerization of the cyclic imino ether (7) has a terminal reactive group. Therefore, the organopolysiloxane of the component (D) can be obtained by reacting the terminal reactive group of poly(N-acylalkyleneimine) with the reactive group represented by the above (viii) to (xiii) of the modified organopolysiloxane represented by the formula (6).

The production method by the living polymerization as described above is effective in that the degree of polymerization can be easily controlled by the amounts of the cyclic imino ether (7) and polymerization initiator used, as shown in the following theoretical formula (II), and also that moreover, almost-monodisperse poly(N-acylalkyleneimine) having a narrower molecular weight distribution than that obtained with common radical polymerization can be obtained.

$$MNi = \frac{\dfrac{\text{Number of moles of cyclic } \textit{imino } \text{ether(7)}}{\text{Number of moles of polymerization initiator}} \times}{\text{Molecular weight of cyclic } \textit{imino } \text{ether(7)} +}$$
$$\text{Molecular weight of polymerization initiator}$$

[ $MNi$; Calculated value of the number average molecular weight of poly($N$-acylalkyleneimine)obtained by living polymerization]

The cyclic imino ether (7) and the polymerization initiator are used preferably in such amounts that MNi in the formula (II) is from 500 to 4000, more preferably in such amounts that MNi in the formula (II) is 800 to 3500, and even more preferably in such amounts that MNi in the formula (II) is from 1000 to 3000.

From the viewpoint of solubility of the obtained organopolysiloxane in a polar solvent such as water and easiness in handling after dissolution, the weight average molecular weight of the modified organopolysiloxane represented by the formula (6) is preferably from 50000 to 150000, more preferably from 70000 to 130000, and even more preferably from 90000 to 110000.

Also, in order to satisfy the mass ratio (a/b) and MWg of the organopolysiloxane of the component (D), an upper limit is placed on the functional group equivalent of the modified organopolysiloxane represented by the formula (6). From this viewpoint as well as the viewpoint of providing the main chain with adequate hydrophobicity, the functional group equivalent is preferably from 10000 to 40000, more preferably from 15000 to 35000, and even more preferably from 18000 to 32000. At this point, the functional group equivalent of the modified organopolysiloxane represented by the formula (6) refers to a value obtained by dividing the weight average molecular weight of the modified organopolysiloxane represented by the formula (6) by the average number of $R^{10}$ per molecule of the modified organopolysiloxane.

From the viewpoint of the elastic modulus and deformation amount of the organopolysiloxane to be obtained, the modified organopolysiloxane represented by the formula (6) and the above terminal reactive poly(N-acylalkyleneimine) are used in such amounts that the mass ratio between them (modified organopolysiloxane/terminal reactive poly(N-acylalkyleneimine)) is in the range of preferably from 80/20 to 95/5, and from the same viewpoint, more preferably from 83/17 to 93/7, and even more preferably from 85/15 to 90/10.

According to the present invention, in the synthesis of each organopolysiloxane, the molecular weights of various molecules were measured in accordance with the following measurement conditions.

<Measurement Conditions for the Weight Average Molecular Weight of Modified Organopolysiloxane>
Column: Super HZ4000+Super HZ2000 (the product of Tosoh Corporation)
Eluent: 1 mM triethylamine/THF
Flow rate: 0.35 mL/min
Column temperature: 40° C.
Detector: UV
Sample: 50 µL
<Measurement Conditions for MNox and MWt>
Column: K-804L (the product of Tosoh Corporation), two columns connected in series were used.
Eluent: 1 mM dimethyl dodecyl.amine/chloroform
Flow rate: 1.0 mL/min
Column temperature: 40° C.
Detector: RI
Sample: 50 µL, Also, the $^1$H-NMR measurement for calculating the mass ratio (a/b) was performed under the following conditions.
<$^1$H-NMR Measurement Conditions>
The composition of the polymer thus obtained was confirmed by $^1$H-NMR (400 MHz, the product of Varian Medical Systems, Inc.).
A solution of 0.5 g of sample in 2 g of measurement solvent (deuterated chloroform) was measured.
Pulse Sequence
Relaxation delay: 30 seconds, Pulse: 45 degrees, Number of scans: 8
Peak confirmed Near 0 ppm: Methyl group in polydimethylsiloxane, Near 3.4 ppm: Methylene moiety in ethyleneimine
The fractions of silicone and poly(N-propionylethyleneimine) were calculated from each integrated value.

Examples of the organopolysiloxane of the component (D) include poly(N-formylethyleneimine)organosiloxane, poly(N-acetylethyleneimine)organosiloxane, and poly(N-propionylethyleneimine) organosiloxane.

The component (D) can be used singly or in combination of two or more thereof, and the content thereof is, relative to the whole cosmetic composition, 0.01% by mass or more, preferably 0.1% by mass or more, and 10% by mass or less, preferably 5% by mass or less so that the resulting cosmetic composition is excellent in attachment to the skin and emulsifiability, and improves the dullness of the skin, allowing the skin to look brighter. Also, the content of the component (D) is preferably from 0.01 to 10% by mass, preferably from 0.1 to 5% by mass of the total composition.

In consideration of the durability of makeup and stability, in the present invention, the mass ratio of component (A) to component (D), (A)/(D), is from 0.1 to 100. The mass ratio of component (A) to component (D), (A)/(D), is preferably 1 or more, more preferably 2 or more, further preferably 4 or more, preferably 60 or less, more preferably 40 or less, and further preferably 15 or less. Also, the mass ratio of component (A) to component (D), (A)/(D), is preferably from 1 to 60, more preferably from 2 to 40, and further preferably from 4 to 15.

In consideration of the feeling upon application and storage stability, the content of water used in the present invention is, relative to the whole cosmetic composition, preferably 10% by mass or more, more preferably 20% by mass or more, and preferably 60% by mass or less, more preferably 50% by mass or less. Also, the water content is preferably from 10 to 60% by mass, more preferably from 20 to 50% by mass of the total composition.

Examples of an oil agent used in the present invention include those remain liquid at 20° C., and when a solid or paste oil agent is used, it is preferable to dissolve it in another oil agent or solvent before use.

Examples of the oil agent used in the present invention include a silicone oil, a hydrocarbon oil, a higher fatty acid, a higher alcohol, an ester oil (including oil and fat), an ether oil, and a mineral oil. From the viewpoint of the feeling upon application, a silicone oil, a hydrocarbon oil, and an ester oil are preferable, of which a silicone oil is more preferable. Among silicone oils, dimethylpolysiloxane and cyclopolysiloxane are more preferable.

These oil agents can be used singly or in combination of two or more thereof.

Also, in consideration of the feeling upon application and storage stability, the content of the oil agent used in the present invention is, relative to the whole cosmetic composition, preferably 10% by mass or more, more preferably 20% by mass or more, and preferably 50% by mass or less, more preferably 40% by mass or less. Also, the content of the oil agent is preferably from 10 to 50% by mass, more preferably from 20 to 40% by mass of the total composition.

Also, examples of a surfactant used in the present invention include an anionic surfactant, a cationic surfactant, am amphoteric surfactant, and a nonionic surfactant. Among them, a nonionic surfactant is preferable, and a polyether-modified silicone is more preferable. From the viewpoint of stably emulsifying the components (A), (B), and (C), the HLB value is preferably 1 or more and 7 or less, more preferably 2 or more and 6 or less.

The content of the surfactant is, relative to the whole cosmetic, preferably 0.1% by mass or more, more preferably 0.2% by mass or more, and preferably 6% by mass or less, more preferably 3% by mass or less. Also, the content of the surfactant is preferably from 0.1 to 6% by mass, more preferably from 0.2 to 3% by mass of the total composition.

At this point, Hydrophilic-Lipophilic Balance (HLB) indicates the proportion of the molecular weight of the hydrophilic group moiety in the total molecular weight of the surfactant, and HLB of a nonionic surfactant can be obtained from the Griffin's formula.

HLB of a mixed surfactant composed of two or more nonionic surfactants can be obtained as follows. HLB of a mixed surfactant is a value obtained by calculating an arithmetic average of the HLB values of individual nonionic surfactants according to their blending ratios.

Mixed HLB=Σ(HLBx×Wx)/ΣWx

HLBx indicates the HLB value of a nonionic surfactant X.

Wx indicates the weight (g) of a nonionic surfactant X having a value of HLBx.

In addition to the above components, the cosmetic composition of the present invention can contain components used in conventional cosmetic compositions, for example, a solid oil component such as Vaseline, lanolin, ceresin, microcrystalline wax, carnauba wax, and candelilla wax; a water-soluble or oil-soluble polymer; a powder other than the components mentioned above; ethanol, polyhydric alcohol, a preservative, an antioxidant, a dye, a thickener, a pH adjustor, a fragrance, an ultraviolet ray absorber, a humectant, a blood circulation-promoter, a cooling agent, an antiperspirant, a disinfectant, and a skin-revitalizing agent.

The cosmetic composition of the present invention can be produced in accordance with a common method, and it can be made into any emulsion type such as a water-in-oil type, an oil-in-water type, and a two-layer separation type. Among them, considering usability, a water-in-oil type emulsified cosmetic composition is preferable. Further, examples of the form include a liquid, an emulsion, a cream, and a gel, among which an emulsion is preferable.

The cosmetic composition of the present invention can be produced in accordance with a common method and provided as, for example, a makeup cosmetic composition such as a liquid foundation, an oil foundation, a powder foundation, a makeup base, a lipstick, a cheek blush, and an eyeshadow; and an ultraviolet protection cosmetic composition such as a sunscreen emulsion and a sunscreen cream. Among them, a liquid foundation, a makeup base, a sunscreen emulsion, and a sunscreen cream are preferable.

Pertaining to the aforementioned embodiments, the present invention further discloses the following compositions, production methods, or usage.

<1> A cosmetic composition, comprising the following components (A), (B), (C), and (D):

(A) from 0.01 to 50% by mass of a fluorine-modified silicone having a polysiloxane unit represented by the following formulae (1) and (2):

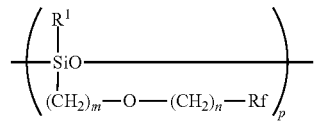

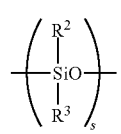

wherein, Rf represents a linear or branched perfluoroalkyl group having 6 carbon atoms; $R^1$, $R^2$, and $R^3$ are the same or different and each represent a linear or branched hydrocarbon group having 1 to 6 carbon atoms; m represents a number of from 2 to 6; n represents a number of from 1 to 6; p represents a number of from 3 to 50; s represents a number of from 1 to 5; and a ratio between p and s satisfies $0.66 \leq p/(p+s) \leq 0.9$, (B) from 0.01 to 40% by mass of a powder having been subjected to a surface treatment with tridecafluoro octyltriethoxysilane, (C) from 0.01 to 20% by mass of a fine zinc oxide particle having a specific surface area of from 10 to 100 m$^2$/g, with the proviso that the component (B) is excluded from the component (C), and (D) from 0.01 to 10% by mass of an organopolysiloxane in which poly(N-acylalkyleneimine) segments are bound to at least two silicon atoms of an organopolysiloxane segment constituting a main chain via alkylene groups each having a hetero atom, the poly(N-acylalkyleneimine) segments comprising a repeating unit represented by the following formula (4):

wherein, $R^4$ represents a hydrogen atom or an alkyl group having 1 to 3 carbon atoms and t represents 2 or 3, wherein, a number average molecular weight of the poly (N-acylalkyleneimine) segment is from 500 to 4000, a mass ratio of (a) the organopolysiloxane segment constituting the main chain to (b) the poly(N-acylalkyleneimine) segment, (a/b), is from 80/20 to 95/5, a weight average molecular weight of the organopolysiloxane segment between adjacent poly(N-acylalkyleneimine) segments is from 10000 to 40000, and a weight average molecular weight of the organopolysiloxane segment constituting the main chain is from 50000 to 150000, and wherein, a mass ratio of the component (A) to the component (D), (A)/(D), is from 0.1 to 100.

<2> The cosmetic composition according to the above <1>, wherein, a content of the component (A) is preferably from 0.1 to 30% by mass, more preferably from 1 to 20% by mass, and even more preferably from 4 to 15% by mass of the total composition.

<3> The cosmetic composition according to the above <1> or <2>, wherein, a content of the component (B) is preferably from 0.1 to 30% by mass, more preferably from 1 to 25% by mass, and even more preferably from 5 to 20% by mass of the total composition.

<4> The cosmetic composition according to any one of the above <1> to <3>, wherein, a mass ratio of the component (A) to the component (B), (A)/(B), is preferably from 0.01 to 50, more preferably from 0.1 to 20, even more preferably from 0.1 to 10, and further preferably from 0.2 to 2.

<5> The cosmetic composition according to any one of the above <1> to <4>, wherein, a content of the component (C) is preferably from 0.1 to 15% by mass, more preferably from 1 to 10% by mass of the total composition.

<6> The cosmetic composition according to any one of the above <1> to <5>, wherein, a mass ratio of the component (A) to the component (C), (A)/(C), is preferably from 0.1 to 10, more preferably from 1 to 7.

<7> The cosmetic composition according to any one of the above <1> to <6>, wherein, a content of the component (D) is preferably from 0.1 to 5% by mass of the total composition.

<8> The cosmetic composition according to any one of the above <1> to <7>, wherein, a mass ratio of the component (A) to the component (D), (A)/(D), is preferably from 1 to 60, more preferably from 2 to 40, and further preferably from 4 to 15.

<9> The cosmetic composition according to any one of the above <1> to <8>, wherein, in the formulae (1) and (2) of the component (A), m is preferably from 2 to 5, more preferably 3; n is preferably from 1 to 4, more preferably 2; p is preferably from 3 to 10, more preferably from 3 to 6; and s is preferably from 1 to 3, more preferably 1.

<10> The cosmetic composition according to any one of the above <1> to <9>, wherein, in the formulae (1) and (2) of the component (A), a ratio of p/(p+s) satisfies preferably 0.66≤p/(p+s)≤0.9, more preferably 0.75≤p/(p+s)≤0.83.

<11> The cosmetic composition according to any one of the above <1> to <10>, wherein, an amount of tridecafluoro octyltriethoxysilane of the component (B) used in the treatment is preferably from 0.05 to 50% by mass, more preferably from 0.1 to 20% by mass.

<12> The cosmetic composition according to any one of the above <1> to <11>, wherein, the component (B) has an average particle diameter of preferably from 0.1 to 20 μm, more preferably from 0.1 to 10 μm.

<13> The cosmetic composition according to any one of the above <1> to <12>, wherein, the component (C) is preferably a fine zinc oxide particle having been subjected to a silicone treatment, more preferably a fine zinc oxide particle having been subjected to a silicone treatment with methyl hydrogen polysiloxane.

<14> The cosmetic composition according to any one of the above <1> to <13>, wherein, the organopolysiloxane of the component (D) is produced by reacting a modified organopolysiloxane with a terminal reactive poly(N-acylalkyleneimine), the modified organopolysiloxane being represented by the following formula (6):

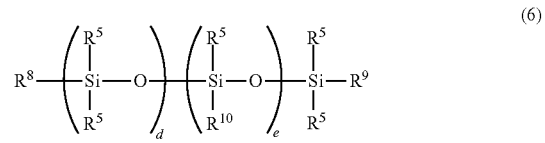

wherein, $R^5$ has the same meaning as above; and $R^8$ and $R^9$ each represent the same group as $R^5$ or a monovalent group represented by any of the following formulae (viii) to (xiii):

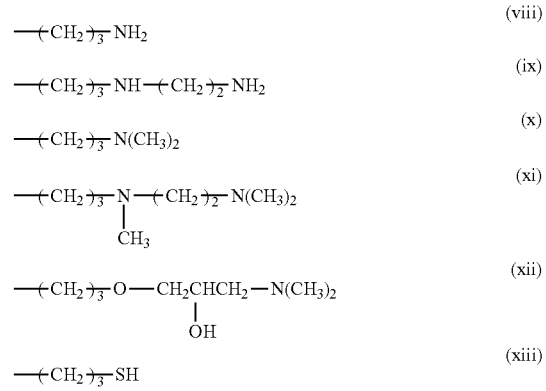

$R^{10}$ represents a monovalent group represented by the above formulae (viii) to (xiii); d represents a number of from 91.5 to 1255.0; and e represents a number of from 2.0 to 62.5; and the terminal reactive poly(N-acylalkyleneimine) being obtainable by ring-opening polymerization of a cyclic imino ether represented by the following formula (7):

wherein, $R^4$ and t have the same meaning as above, and wherein, a mass ratio of the modified organopolysiloxane represented by the formula (6) to the terminal reactive poly(N-acylalkyleneimine), (modified organopolysiloxane/terminal reactive poly(N-acylalkyleneimine)), is preferably from 80/20 to 95/5, more preferably from 83/17 to 93/7, and even more preferably from 85/15 to 90/10.

<15> The cosmetic composition according to any one of the above <1> to <14>, further wherein, a water content is preferably from 10 to 60% by mass, more preferably from 20 to 50% by mass.

<16> The cosmetic composition according to any one of the above <1> to <15>, further comprising an oil agent which is liquid at 20° C., wherein, the oil agent is preferably at least one selected from the group consisting of a silicone oil, a hydrocarbon oil and an ester oil, more preferably a silicone oil, and even more preferably dimethylpolysiloxane or cyclopolysiloxane.

<17> The cosmetic composition according to the above <16>, wherein, a content of the oil agent which is liquid at 20° C. is preferably from 10 to 50% by mass, more preferably from 20 to 40% by mass.

<18> The cosmetic composition according to any one of the above <1> to <17>, further comprising a surfactant, wherein, the surfactant is preferably a nonionic surfactant, more preferably a polyether-modified silicone.
<19> The cosmetic composition according to the above <18>, wherein, the surfactant has an HLB value of preferably 1 or more and 7 or less, more preferably 2 or more and 6 or less.
<20> The cosmetic composition according to the above <18> or <19>, wherein, a content of the surfactant is preferably from 0.1 to 6% by mass, more preferably from 0.2 to 3% by mass.
<21> The cosmetic composition according to any one of the above <1> to <20>, which is preferably a water-in-oil type emulsified cosmetic composition, wherein, the cosmetic composition is preferably in a form of a liquid, an emulsion, a cream, or a gel, more preferably in a form of an emulsion.
<22> The cosmetic composition according to any one of the above <1> to <21>, which is preferably a liquid foundation, a makeup base, a sunscreen emulsion, or a sunscreen cream.

EXAMPLES

Synthetic Example 1

Synthesis of Compound A1

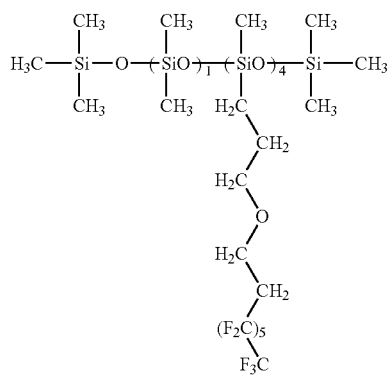

Synthesis of $C_6F_{13}$—$CH_2CH_2$—O—$CH_2CH=CH_2$

Into a 2 L four-necked flask equipped with a thermometer and a condenser pipe, 800 g (2.2 mol) of FA-6 (the product of Unimatec Co., Ltd.) and 175.78 g (4.4 mol) of granular NaOH (the product of Wako Pure Chemical Industries, Ltd.) were added. Under a nitrogen atmosphere, the flask was heated while stirring with a 12 cm crescent stirring blade made of Teflon (registered trade name) at 200 rpm to bring the temperature inside the flask to 60° C. To this flask, 398.73 g (3.3 mol) of allyl bromide (the product of Wako Pure Chemical Industries, Ltd.) was added dropwise over two hours. On completion of the dropwise addition, the resulting mixture was stirred at 70° C. for one hour, then at 80° C. for one hour. Subsequently, the temperature was raised to 130° C. to remove excess allyl bromide. After cooling to 60° C., 800 g of ion-exchanged water was added, followed by stirring for 30 minutes. The flask was then left to stand, and then phase separation was allowed to take place. After removing the resulting upper aqueous layer, 800 g of ion-exchanged water was further added, and the resulting mixture was once again stirred and left to stand, and the resulting aqueous layer was removed. The resulting product was dehydrated at 60° C./5 KPa and distilled at 100° C./2 KPa, whereby 774.9 g (yield 88%) of $C_6F_{13}$—$CH_2CH_2$—O—$CH_2CH=CH_2$ was obtained as a fraction of distillation.

Into a 300 mL four-necked flask equipped with a thermometer, 52.89 g (111 mmol) of hydrogen polysiloxane (the product of Shin-Etsu Chemical Co., Ltd.) represented by the following formula was added, followed by stirring with an 8 cm crescent blade made of Teflon (registered trade name) at 200 rpm under a nitrogen atmosphere. Subsequently, 0.66 g of 2% by mass chloroplatinic acid hexahydrate/isopropyl alcohol was added and the temperature was raised to 110° C.

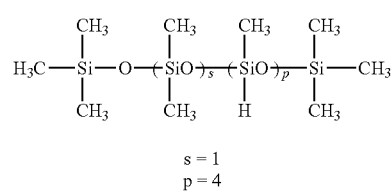

s = 1
p = 4

Then, 197.11 g (488 mmol) of $C_6F_{13}$—$CH_2CH_2$—O—$CH_2CH=CH_2$ was added dropwise over two hours. On completion of the dropwise addition, the resulting mixture was stirred at 110° C. for two hours, and then the temperature was dropped to 70° C. Subsequently, 25.07 g of a 0.1% NaOH solution was added, followed by stirring for two hours. The resulting mixture was dehydrated at 60° C./5 KPa, and on completion of dehydration, at the same temperature, 2.51 g of CARBORAFFIN 3 (the product of Japan EnviroChemicals, Ltd.) was added, followed by stirring for two hours. The resulting solution was filtered through a 0.1 μm PTFE membrane filter and the filtrate thus obtained was subjected to steam distillation with 62.5 g of water at 100° C./5 KPa, whereby 206.3 g (yield 89%) of the compound of interest (Compound A1) was obtained.

Synthetic Example 2

Synthesis of Compound A2

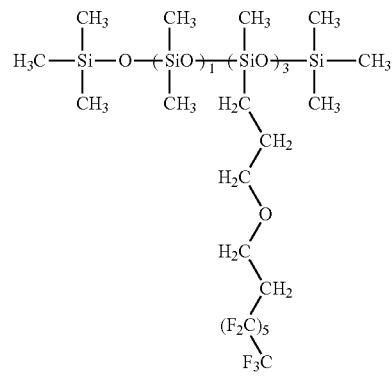

In a similar manner to Synthetic Example 1, $C_6F_{13}$—$CH_2CH_2$—O—$CH_2CH=CH_2$ was synthesized.

Into a 300 mL four-necked flask equipped with a thermometer, 21.29 g (51 mmol) of hydrogen polysiloxane (the product of Shin-Etsu Chemical Co., Ltd.) represented by the following formula was added, followed by stirring with an 8 cm crescent blade made of Teflon (registered trade name) at 200 rpm under a nitrogen atmosphere. Subsequently, 0.26 g of 2% by mass chloroplatinic acid hexahydrate/isopropyl alcohol was added, and the temperature was raised to 110° C.

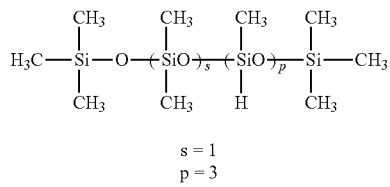

$s = 1$
$p = 3$

Then, 78.71 g (195 mmol) of $C_6F_{13}$—$CH_2CH_2$—O—$CH_2CH$=$CH_2$ was added dropwise over two hours. On completion of the dropwise addition, the resulting mixture was stirred at 110° C. for two hours, and then the temperature was dropped to 70° C. Subsequently, 10.03 g of a 0.1% NaOH solution was added, followed by stirring for two hours. The resulting mixture was dehydrated at 60° C./5 KPa, and on completion of dehydration, at the same temperature, 1.00 g of CARBORAFFIN 3 (the product of Japan EnviroChemicals, Ltd.) was added, followed by stirring for two hours. The resulting solution was filtered through a 0.1 μm PTFE membrane filter and the filtrate thus obtained was subjected to steam distillation with 25 g of water at 100° C./5 KPa, whereby 78.9 g (yield 85%) of the compound of interest (Compound A2) was obtained.

Synthetic Example 3

Synthesis of Compound A3

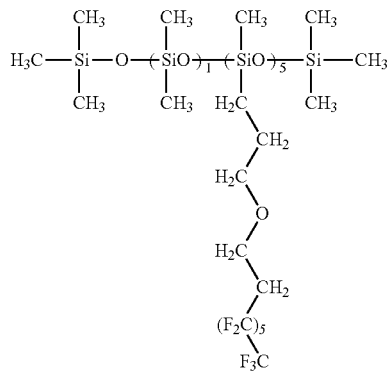

In a similar manner to Synthetic Example 1, $C_6F_{13}$—$CH_2CH_2$—O—$CH_2CH$=$CH_2$ was synthesized.

Into a 300 mL four-necked flask equipped with a thermometer, 17.61 g (33 mmol) of hydrogen polysiloxane (the product of Shin-Etsu Chemical Co., Ltd.) represented by the following formula was added, followed by stirring with an 8 cm crescent blade made of Teflon (registered trade name) at 200 rpm under a nitrogen atmosphere. Subsequently, 0.27 g of 2% by mass chloroplatinic acid hexahydrate/isopropyl alcohol was added, and the temperature was raised to 110° C.

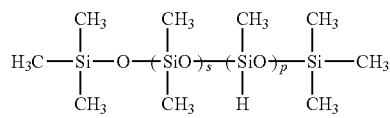

$s = 1$
$p = 5$

Then, 82.39 g (206 mmol) of $C_6F_{13}$—$CH_2CH_2$—O—$CH_2CH$=$CH_2$ was added dropwise over two hours. On completion of the dropwise addition, the resulting mixture was stirred at 110° C. for two hours, and then the temperature was dropped to 70° C. Subsequently, 10.03 g of a 0.1% NaOH solution was added, followed by stirring for two hours. The resulting mixture was dehydrated at 60° C./5 KPa, and on completion of dehydration, at the same temperature, 1.00 g of CARBORAFFIN 3 (the product of Japan EnviroChemicals, Ltd.) was added, followed by stirring for two hours. The resulting solution was filtered through a 0.1 μm PTFE membrane filter and the filtrate thus obtained was subjected to steam distillation with 25 g of water at 100° C./5 KPa, whereby 75.8 g (yield 82%) of the compound of interest (Compound A3) was obtained.

Synthetic Example 4

Synthesis of Compound A4

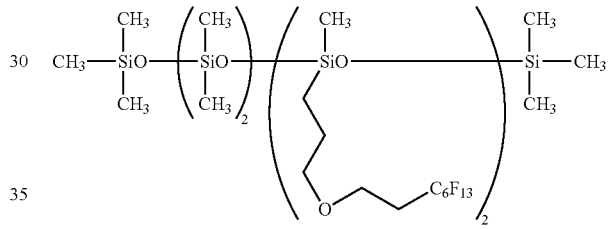

To a 100 mL two-necked flask equipped with a condenser pipe and a magnetic stirrer, under a nitrogen atmosphere, 20 mL of toluene, 8.0 g (18.6 mmol) of hydrogen polysiloxane ($MD_2D_2M^H$) (the product of Toshiba Silicones Co., Ltd.), 18.0 g (44.7 mmol) of $C_6F_{13}$—$CH_2CH_2$—O—$CH_2CH$=$CH_2$, and 29 μL (0.89×10$^{-3}$ mmol) of a 2% solution of chloroplatinic acid in isopropyl alcohol were added, followed by stirring at 110° C. for four hours. The resulting reaction mixture was cooled to room temperature, to which 1.0 g of activated carbon was added, followed by stirring at room temperature for one hour. The activated carbon was filtered out and the solvent was distilled off. After distilling unreacted compounds off under reduced pressure, 20.3 g of the compound of interest (Compound A4) was obtained as a colorless, transparent oily substance (yield 87%).

Synthetic Example 5

Synthesis of Compound A5

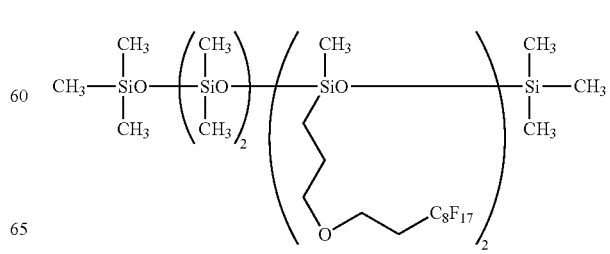

In a 100 mL two-necked flask equipped with a condenser pipe and a magnetic stirrer, under a nitrogen atmosphere, 19.0 g (44.1 mmol) of methyl hydrogen polysiloxane ($MD_2D^H{}_2M$) (the product of Toshiba Silicones Co., Ltd.) and 53.3 g (105.8 mmol) of $C_8F_{17}$—$CH_2CH_2$—O—$CH_2CH$=$CH_2$ were placed. Subsequently, after raising the temperature inside the flask to 80° C., 174.5 µL of a 2% solution of chloroplatinic acid in isopropyl alcohol was added, followed by stirring at 60° C. for five hours. After cooling the resulting reaction mixture to room temperature, 50 mL of hexane and 2.2 g of activated carbon were added, followed by stirring at room temperature for one hour. Subsequently, the activated carbon was filtered out and the solvent was distilled off. Unreacted compounds were then distilled off under reduced pressure, whereby 49.4 g of the compound of interest (Compound A5) was obtained as a colorless, transparent oily substance (yield 78%).

Synthetic Example 6

Synthesis of Compound D1

A mixture obtained by mixing 12.9 g (0.13 mol) of 2-ethyl-2-oxazoline and 27.7 g of ethyl acetate was dehydrated at 28° C. for 15 hours with 2.0 g of a molecular sieve (Zeolum A-4, the product of Tosoh Corporation).

Also, a mixed solution obtained by mixing 100 g of side chain primary aminopropyl-modified polydimethylsiloxane (KF-8015, the product of Shin-Etsu Chemical Co., Ltd., a weight average molecular weight of 100000, an amine equivalent of 20000) and 203 g of ethyl acetate was dehydrated at 28° C. for 15 hours with 15.2 g of a molecular sieve.

To the above dehydrated solution of 2-ethyl-2-oxazoline in ethyl acetate, 0.77 g (0.005 mol) of diethyl sulfate was added, followed by heating to reflux at 80° C. for eight hours under a nitrogen atmosphere, whereby terminal reactive poly(N-propionylethyleneimine) was synthesized. The number average molecular weight as measured by GPC was 2700.

The resulting terminal reactive poly(N-propionylethyleneimine) solution was added to the above dehydrated side chain primary aminopropyl-modified polydimethylsiloxane solution at once, followed by heating to reflux for 10 hours at 80° C.

The resulting reaction mixture was concentrated under reduced pressure, whereby a N-propionylethyleneimine-dimethylsiloxane copolymer was obtained as a white rubber-like solid (108 g). The mass fraction of the organopolysiloxane segment in the final product was 0.87, and the weight average molecular weight of the final product was 115000.

Synthetic Example 7

Synthesis of Compound D2

A mixture obtained by mixing 53.3 g (0.54 mol) of 2-ethyl-2-oxazoline and 127.46 g of ethyl acetate was dehydrated for 15 hours with 9.0 g of a molecular sieve (Zeolum A-4, the product of Tosoh Corporation).

Also, a mixed solution obtained by mixing 153.7 g of side chain primary aminopropyl-modified polydimethylsiloxane (KF-8003, the product of Shin-Etsu Chemical Co., Ltd., a weight average molecular weight of 40000, an amine equivalent of 2000) and 312.06 g of ethyl acetate was dehydrated at 28° C. for 15 hours with 23.29 g of a molecular sieve.

To the above dehydrated solution of 2-ethyl-2-oxazoline in ethyl acetate, 9.48 g (0.061 mol) of diethyl sulfate was added, followed by heating to reflux at 80° C. for 8 hours under a nitrogen atmosphere, whereby terminal reactive poly(N-propionylethyleneimine) was synthesized. The number average molecular weight as measured by GPC was 1300.

The resulting terminal reactive poly(N-propionylethyleneimine) solution was added to the above dehydrated side chain primary aminopropyl-modified polydimethylsiloxane solution at once, followed by heating to reflux for 10 hours at 80° C.

The resulting reaction mixture was concentrated under reduced pressure, whereby a N-propionylethyleneimine-dimethylsiloxane copolymer was obtained as a light yellow rubber-like solid (200 g). The mass fraction of the organopolysiloxane segment in the final product was 0.71, and the weight average molecular weight of the final product was 56000.

Synthetic Example 8

Synthesis of Compound D3

A mixture obtained by mixing 3.63 g (0.036 mol) of 2-ethyl-2-oxazoline and 8.46 g of ethyl acetate was dehydrated for 15 hours at 28° C. with 0.6 g of a molecular sieve (Zeolum A-4, the product of Tosoh Corporation).

Also, a mixed solution obtained by mixing 100 g of side chain primary aminopropyl-modified polydimethylsiloxane (KF-8015, the product of Shin-Etsu Chemical Co., Ltd., a weight average molecular weight of 100000, an amine equivalent of 20000) and 203 g of ethyl acetate was dehydrated at 28° C. for 15 hours with 15.2 g of a molecular sieve.

To the above dehydrated solution of 2-ethyl-2-oxazoline in ethyl acetate, 0.54 g (0.0035 mol) of diethyl sulfate was added, followed by heating to reflux at 80° C. for 8 hours under a nitrogen atmosphere, whereby terminal reactive poly (N-propionylethyleneimine) was synthesized. The number average molecular weight as measured by GPC was 1200.

The resulting terminal reactive poly(N-propionylethyleneimine) solution was added to the above dehydrated side chain primary aminopropyl-modified polydimethylsiloxane solution at once, followed by heating to reflux for 10 hours at 80° C.

The resulting reaction mixture was concentrated under reduced pressure, whereby a N-propionylethyleneimine-dimethylsiloxane copolymer was obtained as a white rubber-like solid (102 g). The mass fraction of the organopolysiloxane segment in the final product was 0.96, and the weight average molecular weight of the final product was 104000.

TABLE 1

|  | Synthetic Example 6 | Synthetic Example 7 | Synthetic Example 8 |
|---|---|---|---|
| MNox | 2700 | 1300 | 1200 |
| MWt | 100000 | 40000 | 100000 |
| Silicone amine equivalent | 20000 | 2000 | 20000 |
| MWg | 20000 | 2500 | 28600 |
| Mass ratio of modified organopolysiloxane/terminal reactive poly(N-acylalkyleneimine) | 87/13 | 71/29 | 96/4 |
| Weight average molecular weight of final product | 115000 | 56000 | 104000 |

Examples 1 to 15 and Comparative Examples 1 to 7

W/O emulsion foundations having the compositions as shown in Tables 2 and 3 were produced, and the "lack of dullness of the skin", "skin brightness", "degree of concealment of pores", "skin texture seems to be even", and "excellence in attachment to the skin" were evaluated. The results are collectively shown in Tables 2 and 3.

(Production Method)

With respect to Examples 1 to 15 and Comparative Examples 1 to 7, the components were weighed out based on a total weight of 100 g. For preliminary dispersion of oil phase, the oil phase (containing an activating agent) containing the component (A) was dispersed using a disperser (500 r/min, 5 minutes). Subsequently, a powder phase containing the components (B) and (C) was dispersed (1500 r/min, 10 minutes) in the oil phase. Homogeneous dispersion of the powder phase was confirmed. To the oil phase in which the powder phase was homogeneously dispersed, an ethanol phase was gradually added while stirring with a propeller (450 r/min). An aqueous phase component was then added over approximately 10 minutes and the resulting mixture was emulsified, and the emulsified state was maintained. Then, the viscosity was adjusted using a homomixer (3000 r/min) and defoaming was performed, whereby W/O emulsion foundations were obtained.

(Evaluation Method)

Fifteen expert panelists evaluated the "lack of dullness of the skin", "skin brightness", "degree of concealment of pores", "skin texture appears to be even", and "excellence in attachment to the skin" immediately after applying each W/O emulsion foundation to the skin using a sponge based on the following criteria. The integrated values of 15 expert panelists are shown in Tables 2 and 3.

(1) Lack of Dullness of the Skin
4; Skin is free from dullness.
3; Skin is not very dull.
2; Skin is slightly dull.
1; Skin is dull.

(2) Skin Brightness
4; Skin seems bright.
3; Skin seems slightly bright.
2; Skin does not seem very bright.
1; Skin does not seem bright.

(3) Degree of Concealment of Pores
4; Pores are not noticeable.
3; Pores are not very noticeable.
2; Pores are slightly noticeable.
1; Pores are noticeable.

(4) Skin Texture Seems to be Even
4; Skin texture seems to be even.
3; Skin texture seems to be slightly even.
2; Skin texture seems to be poorly even.
1; Skin texture does not seem to be even.

(5) Excellence in Attachment to the Skin;
4; Excellent attachment to the skin.
3; Slightly excellent attachment to the skin.
2; Slightly poor attachment to the skin.
1; Poor attachment to the skin.

TABLE 2

| | | Component (% by mass) | Example 1 | Example 2 | Example 3 | Example 4 | Example 5 | Example 6 |
|---|---|---|---|---|---|---|---|---|
| Oil phase | (A) | Fluorine-modified silicone (Synthetic Example 1) | 7.0 | — | — | 4.0 | 15.0 | 7.0 |
| | | Fluorine-modified silicone (Synthetic Example 2) | — | 7.0 | — | — | — | — |
| | | Fluorine-modified silicone (Synthetic Example 3) | — | — | 7.0 | — | — | — |
| | Other components | Fluorine-modified silicone (Synthetic Example 4) | — | — | — | — | — | — |
| | | Fluorine-modified silicone (Synthetic Example 5) | — | — | — | — | — | — |
| Powder phase | (B) | Titanium oxide treated with 5% by mass tridecafluoro octyltriethoxysilane | 7.5 | 7.5 | 7.5 | 7.5 | 7.5 | 7.5 |
| | | Red iron oxide treated with 5% by mass tridecafluoro octyltriethoxysilane | 0.4 | 0.4 | 0.4 | 0.4 | 0.4 | 0.4 |
| | | Yellow iron oxide treated with 5% by mass tridecafluoro octyltriethoxysilane | 2.0 | 2.0 | 2.0 | 2.0 | 2.0 | 2.0 |
| | | Black iron oxide treated with 5% by mass tridecafluoro octyltriethoxysilane | 0.1 | 0.1 | 0.1 | 0.1 | 0.1 | 0.1 |
| | | Titanium mica treated with 3% by mass tridecafluoro octyltriethoxysilane | 4.0 | 4.0 | 4.0 | 4.0 | 4.0 | 4.0 |
| | | Nylon powder treated with 5% by mass tridecafluoro octyltriethoxysilane | 2.0 | 2.0 | 2.0 | 2.0 | 2.0 | 2.0 |
| | | Plate-like silica enclosing titanium treated with 3% by mass tridecafluoro octyltriethoxysilane (containing 30% by mass Titanium oxide) | 1.0 | 1.0 | 1.0 | 1.0 | 1.0 | 1.0 |
| | Other components | Titanium oxide treated with 5% by mass perfluoroalkyl phosphate ester | — | — | — | — | — | — |
| | | Red iron oxide treated with 5% by mass perfluoroalkyl phosphate ester | — | — | — | — | — | — |
| | | Yellow iron oxide treated with 5% by mass perfluoroalkyl phosphate ester | — | — | — | — | — | — |
| | | Black iron oxide treated with 5% by mass perfluoroalkyl phosphate ester | — | — | — | — | — | — |
| | | Titanium mica treated with 3% by mass perfluoroalkyl phosphate ester | — | — | — | — | — | — |
| | | Nylon powder treated with 5% by mass perfluoroalkyl phosphate ester | — | — | — | — | — | — |
| | | Plate-like silica enclosing titanium treated with 3% by mass perfluoroalkyl phosphate ester (containing 30% by mass Titanium oxide) | — | — | — | — | — | — |
| | (C) | Fine zinc oxide particles treated with 6% by mass silicone (FINEX-50, specific surface area 45 $m^2/g$) | 3.0 | 3.0 | 3.0 | 3.0 | 3.0 | 1.0 |

TABLE 2-continued

| | | | | | | | | |
|---|---|---|---|---|---|---|---|---|
| Ethanol phase | (D) | Oxazoline-modified silicone (Synthetic Example 6) | 1.0 | 1.0 | 1.0 | 1.0 | 1.0 | 1.0 |
| | | Oxazoline-modified silicone (Synthetic Example 7) | — | — | — | — | — | — |
| | | Oxazoline-modified silicone (Synthetic Example 8) | — | — | — | — | — | — |
| | | Ethanol | 6.0 | 6.0 | 6.0 | 6.0 | 6.0 | 6.0 |
| Oil phase | Other components | Dimethylpolysiloxane-polyoxyalkylene copolymer (Dow Corning Toray Co., Ltd., Silicone SH3775M) | 0.5 | 0.5 | 0.5 | 0.5 | 0.5 | 0.5 |
| | | Decamethylcyclopentasiloxane (the product of Dow Corning Toray Co., Ltd., SH245) | 15.0 | 15.0 | 15.0 | 15.0 | 15.0 | 15.0 |
| | | Dimethylpolysiloxane (Dow Corning Toray Co., Ltd., Silicone SH200 C Fluid 2CS) | 15.0 | 15.0 | 15.0 | 15.0 | 15.0 | 15.0 |
| Aqueous phase | | Magnesium sulfate | 0.7 | 0.7 | 0.7 | 0.7 | 0.7 | 0.7 |
| | | Glycerol | 1.0 | 1.0 | 1.0 | 1.0 | 1.0 | 1.0 |
| | | Purified water | Balance | Balance | Balance | Balance | Balance | Balance |
| | | Total | 100 | 100 | 100 | 100 | 100 | 100 |
| | | Sum of (B) | 17 | 17 | 17 | 17 | 17 | 17 |
| | | (A)/(B) | 0.41 | 0.41 | 0.41 | 0.24 | 0.88 | 0.41 |
| | | (A)/(C) | 2.3 | 2.3 | 2.3 | 1.3 | 5.0 | 7.0 |
| | | (A)/(D) | 7 | 7 | 7 | 4 | 15 | 7 |
| Effect | | Lack of dullness of the skin | 51 | 45 | 43 | 39 | 44 | 42 |
| | | Skin brightness | 46 | 44 | 43 | 44 | 42 | 45 |
| | | Degree of concealment of pores | 51 | 47 | 45 | 41 | 40 | 37 |
| | | Skin texture seems to be even | 48 | 50 | 45 | 40 | 38 | 40 |
| | | Excellence in attachment to the skin | 47 | 40 | 51 | 43 | 38 | 45 |

| | | | Example | | | | |
|---|---|---|---|---|---|---|---|
| | | Component (% by mass) | 7 | 8 | 9 | 10 | 11 |
| Oil phase | (A) | Fluorine-modified silicone (Synthetic Example 1) | 7.0 | 7.0 | 7.0 | 1.7 | 30.0 |
| | | Fluorine-modified silicone (Synthetic Example 2) | — | — | — | — | — |
| | | Fluorine-modified silicone (Synthetic Example 3) | — | — | — | — | — |
| | Other components | Fluorine-modified silicone (Synthetic Example 4) | — | — | — | — | — |
| | | Fluorine-modified silicone (Synthetic Example 5) | — | — | — | — | — |
| Powder phase | (B) | Titanium oxide treated with 5% by mass tridecafluoro octyltriethoxysilane | 7.5 | 2.17 | 8.9 | 7.5 | 7.5 |
| | | Red iron oxide treated with 5% by mass tridecafluoro octyltriethoxysilane | 0.4 | 0.1 | 0.5 | 0.4 | 0.4 |
| | | Yellow iron oxide treated with 5% by mass tridecafluoro octyltriethoxysilane | 2.0 | 0.6 | 2.3 | 2.0 | 2.0 |
| | | Black iron oxide treated with 5% by mass tridecafluoro octyltriethoxysilane | 0.1 | 0.03 | 0.1 | 0.1 | 0.1 |
| | | Titanium mica treated with 3% by mass tridecafluoro octyltriethoxysilane | 4.0 | 1.2 | 4.7 | 4.0 | 4.0 |
| | | Nylon powder treated with 5% by mass tridecafluoro octyltriethoxysilane | 2.0 | 0.6 | 2.3 | 2.0 | 2.0 |
| | | Plate-like silica enclosing titanium treated with 3% by mass tridecafluoro octyltriethoxysilane (containing 30% by mass Titanium oxide) | 1.0 | 0.3 | 1.2 | 1.0 | 1.0 |
| | Other components | Titanium oxide treated with 5% by mass perfluoroalkyl phosphate ester | — | — | — | — | — |
| | | Red iron oxide treated with 5% by mass perfluoroalkyl phosphate ester | — | — | — | — | — |
| | | Yellow iron oxide treated with 5% by mass perfluoroalkyl phosphate ester | — | — | — | — | — |
| | | Black iron oxide treated with 5% by mass perfluoroalkyl phosphate ester | — | — | — | — | — |
| | | Titanium mica treated with 3% by mass perfluoroalkyl phosphate ester | — | — | — | — | — |
| | | Nylon powder treated with 5% by mass perfluoroalkyl phosphate ester | — | — | — | — | — |
| | | Plate-like silica enclosing titanium treated with 3% by mass perfluoroalkyl phosphate ester (containing 30% by mass Titanium oxide) | — | — | — | — | — |
| | (C) | Fine zinc oxide particles treated with 6% by mass silicone (FINEX-50, specific surface area 45 m²/g) | 10.0 | 3.0 | 3.0 | 3.0 | 3.0 |
| Ethanol phase | (D) | Oxazoline-modified silicone (Synthetic Example 6) | 1.0 | 1.0 | 1.0 | 1.0 | 1.0 |
| | | Oxazoline-modified silicone (Synthetic Example 7) | — | — | — | — | — |
| | | Oxazoline-modified silicone (Synthetic Example 8) | — | — | — | — | — |
| | | Ethanol | 6.0 | 6.0 | 6.0 | 6.0 | 6.0 |
| Oil phase | Other components | Dimethylpolysiloxane-polyoxyalkylene copolymer (Dow Corning Toray Co., Ltd., Silicone SH3775M) | 0.5 | 0.5 | 0.5 | 0.5 | 0.5 |
| | | Decamethylcyclopentasiloxane (the product of Dow Corning Toray Co., Ltd., SH245) | 15.0 | 15.0 | 15.0 | 15.0 | 15.0 |
| | | Dimethylpolysiloxane (Dow Corning Toray Co., Ltd., Silicone SH200 C Fluid 2CS) | 15.0 | 15.0 | 15.0 | 15.0 | 15.0 |

TABLE 2-continued

|  |  |  |  |  |  |  |
|---|---|---|---|---|---|---|
| Aqueous phase | Magnesium sulfate | 0.7 | 0.7 | 0.7 | 0.7 | 0.7 |
|  | Glycerol | 1.0 | 1.0 | 1.0 | 1.0 | 1.0 |
|  | Purified water | Balance | Balance | Balance | Balance | Balance |
|  | Total | 100 | 100 | 100 | 100 | 100 |
|  | Sum of (B) | 17 | 5 | 20 | 17 | 17 |
|  | (A)/(B) | 0.41 | 1.40 | 0.35 | 0.10 | 1.76 |
|  | (A)/(C) | 0.7 | 2.3 | 2.3 | 0.6 | 10.0 |
|  | (A)/(D) | 7 | 7 | 7 | 2 | 30 |
| Effect | Lack of dullness of the skin | 41 | 41 | 47 | 37 | 40 |
|  | Skin brightness | 43 | 39 | 45 | 42 | 38 |
|  | Degree of concealment of pores | 45 | 39 | 48 | 39 | 47 |
|  | Skin texture seems to be even | 43 | 40 | 45 | 38 | 34 |
|  | Excellence in attachment to the skin | 38 | 44 | 38 | 41 | 34 |

TABLE 3

|  |  |  | Example |  |  |  | Comparative Example |  |
|---|---|---|---|---|---|---|---|---|
|  |  | Component (% by mass) | 12 | 13 | 14 | 15 | 1 | 2 |
| Oil phase | (A) | Fluorine-modified silicone (Synthetic Example 1) | 7.0 | 7.0 | 7.0 | 7.0 | 7.0 | — |
|  |  | Fluorine-modified silicone (Synthetic Example 2) | — | — | — | — | — | — |
|  |  | Fluorine-modified silicone (Synthetic Example 3) | — | — | — | — | — | — |
|  | Other components | Fluorine-modified silicone (Synthetic Example 4) | — | — | — | — | — | 7.0 |
|  |  | Fluorine-modified silicone (Synthetic Example 5) | — | — | — | — | — | — |
| Powder phase | (B) | Titanium oxide treated with 5% by mass tridecafluoro octyltriethoxysilane | 0.375 | 7.5 | 7.5 | 7.5 | — | 7.5 |
|  |  | Red iron oxide treated with 5% by mass tridecafluoro octyltriethoxysilane | 0.020 | 0.4 | 0.4 | 0.4 | — | 0.4 |
|  |  | Yellow iron oxide treated with 5% by mass tridecafluoro octyltriethoxysilane | 0.100 | 2.0 | 2.0 | 2.0 | — | 2.0 |
|  |  | Black iron oxide treated with 5% by mass tridecafluoro octyltriethoxysilane | 0.050 | 0.1 | 0.1 | 0.1 | — | 0.1 |
|  |  | Titanium mica treated with 3% by mass tridecafluoro octyltriethoxysilane | 0.200 | 4.0 | 4.0 | 4.0 | — | 4.0 |
|  |  | Nylon powder treated with 5% by mass tridecafluoro octyltriethoxysilane | 0.100 | 2.0 | 2.0 | 2.0 | — | 2.0 |
|  |  | Plate-like silica enclosing titanium treated with 3% by mass tridecafluoro octyltriethoxysilane (containing 30% by mass Titanium oxide) | 0.050 | 1.0 | 1.0 | 1.0 | — | 1.0 |
|  | Other components | Titanium oxide treated with 5% by mass perfluoroalkyl phosphate ester | — | — | — | — | 7.5 | — |
|  |  | Red iron oxide treated with 5% by mass perfluoroalkyl phosphate ester | — | — | — | — | 0.4 | — |
|  |  | Yellow iron oxide treated with 5% by mass perfluoroalkyl phosphate ester | — | — | — | — | 2.0 | — |
|  |  | Black iron oxide treated with 5% by mass perfluoroalkyl phosphate ester | — | — | — | — | 0.1 | — |
|  |  | Titanium mica treated with 3% by mass perfluoroalkyl phosphate ester | — | — | — | — | 4.0 | — |
|  |  | Nylon powder treated with 5% by mass perfluoroalkyl phosphate ester | — | — | — | — | 2.0 | — |
|  |  | Plate-like silica enclosing titanium treated with 3% by mass perfluoroalkyl phosphate ester (containing 30% by mass Titanium oxide) | — | — | — | — | 1.0 | — |
|  | (C) | Fine zinc oxide particles treated with 6% by mass silicone (FINEX-50, specific surface area 45 m$^2$/g) | 3.0 | 20.0 | 3.0 | 3.0 | 3.0 | 3.0 |
| Ethanol phase | (D) | Oxazoline-modified silicone (Synthetic Example 6) | 1.0 | 1.0 | 0.2 | 3.0 | 1.0 | 1.0 |
|  |  | Oxazoline-modified silicone (Synthetic Example 7) | — | — | — | — | — | — |
|  |  | Oxazoline-modified silicone (Synthetic Example 8) | — | — | — | — | — | — |
|  |  | Ethanol | 6.0 | 6.0 | 6.0 | 6.0 | 6.0 | 6.0 |
| Oil phase | Other components | Dimethylpolysiloxane-polyoxyalkylene copolymer (Dow Corning Toray Co., Ltd., Silicone SH3775M) | 0.5 | 0.5 | 0.5 | 0.5 | 0.5 | 0.5 |
|  |  | Decamethylcyclopentasiloxane (the product of Dow Corning Toray Co., Ltd., SH245) | 15.0 | 15.0 | 15.0 | 15.0 | 15.0 | 15.0 |
|  |  | Dimethylpolysiloxane (the product of Dow Corning Toray Co., Ltd., Silicone SH200 C Fluid 2CS) | 15.0 | 15.0 | 15.0 | 15.0 | 15.0 | 15.0 |

TABLE 3-continued

|  |  | Component (% by mass) | | | | | |
|---|---|---|---|---|---|---|---|
| Aqueous phase | | Magnesium sulfate | 0.7 | 0.7 | 0.7 | 0.7 | 0.7 | 0.7 |
| | | Glycerol | 1.0 | 1.0 | 1.0 | 1.0 | 1.0 | 1.0 |
| | | Purified water | Balance | Balance | Balance | Balance | Balance | Balance |
| | | Total | 100 | 100 | 100 | 100 | 100 | 100 |
| | | Sum of (B) | 1 | 17 | 17 | 17 | 0 | 17 |
| | | (A)/(B) | 7.82 | 0.41 | 0.41 | 0.41 | — | — |
| | | (A)/(C) | 2.3 | 0.4 | 2.3 | 2.3 | 2.3 | — |
| | | (A)/(D) | 7 | 7 | 35 | 2 | 7 | — |
| Effect | | Lack of dullness of the skin | 39 | 39 | 48 | 52 | 33 | 34 |
| | | Skin brightness | 37 | 41 | 43 | 48 | 32 | 34 |
| | | Degree of concealment of pores | 37 | 41 | 48 | 52 | 35 | 29 |
| | | Skin texture seems to be fixed | 38 | 42 | 45 | 50 | 33 | 32 |
| | | Excellence in attachment to the skin | 42 | 36 | 44 | 52 | 38 | 34 |

|  |  |  | Comparative Example | | | | |
|---|---|---|---|---|---|---|---|
|  |  | Component (% by mass) | 3 | 4 | 5 | 6 | 7 |
| Oil phase | (A) | Fluorine-modified silicone (Synthetic Example 1) | — | — | — | 7.0 | 7.0 |
| | | Fluorine-modified silicone (Synthetic Example 2) | — | — | — | — | — |
| | | Fluorine-modified silicone (Synthetic Example 3) | — | — | — | — | — |
| | Other components | Fluorine-modified silicone (Synthetic Example 4) | 7.0 | — | — | — | — |
| | | Fluorine-modified silicone (Synthetic Example 5) | — | 7.0 | 7.0 | — | — |
| Powder phase | (B) | Titanium oxide treated with 5% by mass tridecafluoro octyltriethoxysilane | — | 7.5 | — | 7.5 | 7.5 |
| | | Red iron oxide treated with 5% by mass tridecafluoro octyltriethoxysilane | — | 0.4 | — | 0.4 | 0.4 |
| | | Yellow iron oxide treated with 5% by mass tridecafluoro octyltriethoxysilane | — | 2.0 | — | 2.0 | 2.0 |
| | | Black iron oxide treated with 5% by mass tridecafluoro octyltriethoxysilane | — | 0.1 | — | 0.1 | 0.1 |
| | | Titanium mica treated with 3% by mass tridecafluoro octyltriethoxysilane | — | 4.0 | — | 4.0 | 4.0 |
| | | Nylon powder treated with 5% by mass tridecafluoro octyltriethoxysilane | — | 2.0 | — | 2.0 | 2.0 |
| | | Plate-like silica enclosing titanium treated with 3% by mass tridecafluoro octyltriethoxysilane (containing 30% by mass Titanium oxide) | — | 1.0 | — | 1.0 | 1.0 |
| | Other components | Titanium oxide treated with 5% by mass perfluoroalkyl phosphate ester | 7.5 | — | 7.5 | — | — |
| | | Red iron oxide treated with 5% by mass perfluoroalkyl phosphate ester | 0.4 | — | 0.4 | — | — |
| | | Yellow iron oxide treated with 5% by mass perfluoroalkyl phosphate ester | 2.0 | — | 2.0 | — | — |
| | | Black iron oxide treated with 5% by mass perfluoroalkyl phosphate ester | 0.1 | — | 0.1 | — | — |
| | | Titanium mica treated with 3% by mass perfluoroalkyl phosphate ester | 4.0 | — | 4.0 | — | — |
| | | Nylon powder treated with 5% by mass perfluoroalkyl phosphate ester | 2.0 | — | 2.0 | — | — |
| | | Plate-like silica enclosing titanium treated with 3% by mass perfluoroalkyl phosphate ester (containing 30% by mass Titanium oxide) | 1.0 | — | 1.0 | — | — |
| | (C) | Fine zinc oxide particles treated with 6% by mass silicone (FINEX-50, specific surface area 45 m$^2$/g) | 3.0 | 3.0 | 3.0 | 3.0 | 3.0 |
| Ethanol phase | (D) | Oxazoline-modified silicone (Synthetic Example 6) | 1.0 | 1.0 | 1.0 | — | — |
| | | Oxazoline-modified silicone (Synthetic Example 7) | — | — | — | 1.0 | — |
| | | Oxazoline-modified silicone (Synthetic Example 8) | — | — | — | — | 1.0 |
| | | Ethanol | 6.0 | 6.0 | 6.0 | 6.0 | 6.0 |
| Oil phase | Other components | Dimethylpolysiloxane-polyoxyalkylene copolymer (Dow Corning Toray Co., Ltd., Silicone SH3775M) | 0.5 | 0.5 | 0.5 | 0.5 | 0.5 |
| | | Decamethylcyclopentasiloxane (the product of Dow Corning Toray Co., Ltd., SH245) | 15.0 | 15.0 | 15.0 | 15.0 | 15.0 |
| | | Dimethylpolysiloxane (the product of Dow Corning Toray Co., Ltd., Silicone SH200 C Fluid 2CS) | 15.0 | 15.0 | 15.0 | 15.0 | 15.0 |
| Aqueous phase | | Magnesium sulfate | 0.7 | 0.7 | 0.7 | 0.7 | 0.7 |
| | | Glycerol | 1.0 | 1.0 | 1.0 | 1.0 | 1.0 |
| | | Purified water | Balance | Balance | Balance | Balance | Balance |
| | | Total | 100 | 100 | 100 | 100 | 100 |
| | | Sum of (B) | 0 | 17 | 0 | 17 | 17 |
| | | (A)/(B) | — | — | — | 0.41 | 0.41 |
| | | (A)/(C) | — | — | — | 2.3 | 2.3 |
| | | (A)/(D) | — | — | — | — | — |

TABLE 3-continued

| Effect | | | | | | |
|---|---|---|---|---|---|---|
| Lack of dullness of the skin | 32 | 33 | 30 | 37 | 34 |
| Skin brightness | 27 | 29 | 33 | 34 | 37 |
| Degree of concealment of pores | 31 | 29 | 33 | 24 | 28 |
| Skin texture seems to be fixed | 35 | 29 | 37 | 21 | 27 |
| Excellence in attachment to the skin | 33 | 36 | 34 | 36 | 36 |

Example 16

Cream Foundation (Composition)

| | | |
|---|---|---|
| (1) | α-Monoalkyl glyceryl ether (HLB 1.8) | 1.0 (% by mass) |
| (2) | Dimethylsiloxane-methyl(undecyl glyceryl ether)siloxane copolymer (described in JP-A-4-108795) | 1.0 |
| (3) | Dimethylpolysiloxane-polyoxyalkylene copolymer (product of Shin-Etsu Chemical Co., Ltd., Silicone KF-6015) | 1.0 |
| (4) | Fluorine-modified silicone (Synthetic Example 1) | 6.0 |
| (5) | Decamethylcyclopentasiloxane (product of Dow Corning Toray Co., Ltd., Silicone SH245) | 15.0 |
| (6) | Dimethylpolysiloxane (product of Shin-Etsu Chemical Co., Ltd., KF-96L2CS) | 20.0 |
| (7) | Dimethylpolysiloxane (product of Shin-Etsu Chemical Co., Ltd., KF-96A5CS) | 3.0 |
| (8) | 2-ethylhexyl para-methoxycinnamate | 2.0 |
| (9) | Fragrance | trace |
| (10) | Oxazoline-modified silicone (Synthetic Example 6) | 1.0 |
| (11) | Ethanol | 2.0 |
| (12) | 1,3-Butylene glycol | 2.0 |
| (13) | 86% Glycerol | 5.0 |
| (14) | Purified water | balance |
| (15) | Preservative | q.s. |
| (16) | Titanium oxide treated with 5% by mass FHS | 8.0 |
| (17) | Red iron oxide treated with 5% by mass FHS | 0.9 |
| (18) | Yellow iron oxide treated with 5% by mass FHS | 3.0 |
| (19) | Black iron oxide treated with 5% by mass FHS | 0.1 |
| (20) | Silica enclosing titanium treated with 3% by mass FHS (titanium content 30%) | 3.0 |
| (21) | Tospearl treated with 5% by mass FHS | 4.0 |
| (22) | Talc 5% by mass FHS | 5.0 |
| (23) | Fine zinc oxide particle treated with silicone (Silicone-treated FINEX-M, specific surface area 40 m²/g) | 5.0 |
| Total | | 100 |

(Production Method)

After roughly mixing the powder components (16) to (23), the resulting powder mixture was mixed and ground by an atomizer grinding machine (the product of Fuji Paudal Co., Ltd.). The oil phase components (1) to (9) were mixed by stirring, to which the ground powder components were added, followed by dispersion using a disperser. The components (10) and (11) were mixed by stirring and then added to the oil phase components. Further, the aqueous phase components (12) to (15) were mixed and then added to the oil phase components, followed by emulsification. The viscosity was then adjusted by a homomixer, whereby a cream foundation was obtained.

Example 17

Makeup Base (Composition)

| | | |
|---|---|---|
| (1) | Dimethylpolysiloxane-polyoxyalkylene copolymer (product of Shin-Etsu Chemical Co., Ltd., KF-6016) | 0.4 (% by mass) |
| (2) | Fluorine-modified silicone (Synthetic Example 2) | 12.0 |
| (3) | Decamethylcyclopentapolysiloxane (product of Dow Corning Toray Co., Ltd., SH245) | 15.0 |
| (4) | Decamethyltetrasiloxane (product of Shin-Etsu Chemical Co., Ltd., KF-96L1.5CS) | 15.0 |
| (5) | Dimethylpolysiloxane (product of Shin-Etsu Chemical Co., Ltd., KF-96L2CS) | 10.0 |
| (6) | 2-ethylhexyl para-methoxycinnamate | 0.5 |
| (7) | Glycerol | 1.0 |
| (8) | Purified water | balance |
| (9) | Oxazoline-modified silicone (Synthetic Example 6) | 1.0 |
| (10) | Ethanol | 5.0 |
| (11) | Talc treated with 3% by mass FHS | 2.0 |
| (12) | Nylon powder treated with 5% by mass FHS | 2.0 |
| (13) | Silica enclosing titanium treated with 3% by mass FHS (titanium content 30%) | 2.0 |
| (14) | Fine zinc oxide particles treated with silicone (MICRO ZINC OXIDE MZ-504R3M, specific surface area 40 m²/g) | 3.0 |
| Total | | 100 |

(Production Method)

After roughly mixing the powder components (12) to (15), the resulting powder mixture was mixed and ground by an atomizer grinding machine (the product of Fuji Paudal Co., Ltd.). The oil phase components (1) to (7) were mixed by stirring, to which the ground powder components were added, followed by dispersion using a disperser. The components (10) and (11) were mixed by stirring and then added to the oil phase components. Further, the aqueous phase components (8) to (9) were mixed and then added to the oil phase components, followed by emulsification. The viscosity was then adjusted by a homomixer, whereby a makeup base was obtained.

Both of the cosmetic compositions obtained in Examples 16 and 17 can improve the dullness of the skin, create a makeup finish with bright skin, make pores less noticeable, and create even skin texture. Moreover, these cosmetics had excellent attachment to the skin.

Example 18

Sunscreen Cosmetic Composition (Composition)

| | | |
|---|---|---|
| (1) | Dimethylpolysiloxane-polyoxyalkylene copolymer (product of Shin-Etsu Chemical Co., Ltd., ES-5612) | 0.7 (% by mass) |
| (1) | Dimethylpolysiloxane-polyoxyalkylene copolymer (product of Shin-Etsu Chemical Co., Ltd., KF-6015) | 0.2 |
| (3) | Fluorine-modified silicone (Synthetic Example 1) | 8.0 |
| (4) | Decamethylcyclopentapolysiloxane (product of Momentive Performance Materials Inc., TSF405A) | 15.0 |
| (5) | Decamethyltetrasiloxane (product of Shin-Etsu Chemical Co., Ltd., KF-96L1.5CS) | 3.0 |
| (6) | Dimethylpolysiloxane (product of Shin-Etsu Chemical Co., Ltd., KF-96L2CS) | 15.0 |
| (7) | Dimethylpolysiloxane (product of Dow Corning Toray Co., Ltd., SH200C Fluid 5CS) | 3.0 |
| (8) | 2-Ethylhexyl para-methoxycinnamate | 6.0 |
| (9) | Glycerol | 2.0 |
| (10) | Dipropylene glycol | 1.0 |
| (11) | Purified water | balance |
| (12) | Oxazoline-modified silicone (Synthetic Example 6) | 1.5 |
| (13) | Ethanol | 5.0 |
| (14) | Talc treated with 3% by mass FHS (JA-46R) | 1.0 |
| (15) | Urethane powder treated with 5% by mass FHS | 2.0 |
| (16) | Silica enclosing titanium treated with 3% by mass FHS (titanium 30%) | 2.0 |
| (17) | Fine titanium oxide particles treated with 3% by mass FHS | 5.0 |
| (18) | Fine zinc oxide particles treated with silicone (MICRO ZINC OXIDE MZ-504R3M, specific surface area 40 m²/g) | 5.0 |
| Total | | 100 |

(Production Method)

After roughly mixing the powder components (14) to (18), the resulting powder mixture was mixed and ground by an atomizer grinding machine (the product of Fuji Paudal Co., Ltd.). The oil phase components (1) to (8) were mixed by stirring, to which the ground powder components were added, followed by dispersion using a disperser. The components (12) and (13) were mixed by stirring and then added to the oil phase components. Further, the aqueous phase components (9) to (11) were mixed and then added to the oil phase components, followed by emulsification. The viscosity was then adjusted by a homomixer, whereby a sunscreen cosmetic composition was obtained.

The sunscreen cosmetic composition obtained in Example 18 has an excellent ultraviolet prevention effect, and moreover, can improve the dullness of the skin, create a makeup finish with bright skin, make pores less noticeable, and create even skin texture. Furthermore, this cosmetic composition had excellent attachment to the skin.

The invention claimed is:

1. A cosmetic composition, comprising components (A), (B), (C), and (D):
   (A) from 0.01 to 50% by mass of a fluorine-modified silicone having a polysiloxane unit represented by formulae (1) and (2):

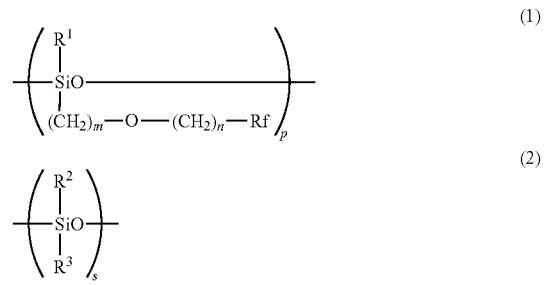

wherein,

Rf represents a linear or branched perfluoroalkyl group having 6 carbon atoms;

$R^1$, $R^2$, and $R^3$ are the same or different and each represent a linear or branched hydrocarbon group having 1 to 6 carbon atoms;

m represents a number of from 2 to 6;

n represents a number of from 1 to 6;

p represents a number of from 3 to 50; s represents a number of from 1 to 5; and a ratio between p and s satisfies $0.66 \leq p/(p+s) \leq 0.9$, (B) from 0.01 to 40% by mass of a powder having been subjected to a surface treatment with tridecafluoro octyltriethoxysilane, (C) from 0.01 to 20% by mass of fine zinc oxide particles having a specific surface area of from 10 to 100 m²/g, with the proviso that the component (B) is excluded from the component (C), and (D) from 0.01 to 10% by mass of an organopolysiloxane in which poly(N-acylalkyleneimine) segments are bound to at least two silicon atoms of an organopolysiloxane segment constituting a main chain via alkylene groups each having a hetero atom, the poly(N-acylalkyleneimine) segments comprising a repeating unit represented by formula (4):

wherein, $R^4$ represents a hydrogen atom or an alkyl group having 1 to 3 carbon atoms and t represents 2 or 3, wherein, a number average molecular weight of the poly(N-acylalkyleneimine) segment is from 500 to 4000, a mass ratio of (a) the organopolysiloxane segment constituting the main chain to (b) the poly(N-acylalkyleneimine) segment, (a/b), is from 80/20 to 95/5, a weight average molecular weight of the organopolysiloxane segment between adjacent poly(N-acylalkyleneimine) segments is from 10000 to 40000, and a weight average molecular weight of the organopolysiloxane segment constituting the main chain is from 50000 to 150000, and wherein, a mass ratio of the component (A) to the component (D), (A)/(D), is from 2 to 40.

2. The cosmetic composition according to claim 1, comprising the component (A) at 1 to 30% by mass, the component (B) at 1 to 20% by mass, the component (C) at 1 to 20% by mass, and the component (D) at 0.1 to 5% by mass of the total composition.

3. The cosmetic composition according to claim 1, wherein, a mass ratio of the component (A) to the component (C), (A)/(C), is from 0.1 to 10.

4. The cosmetic composition according to claim 1, wherein, a mass ratio of the component (A) to the component (B), (A)/(B), is from 0.01 to 50.

5. The cosmetic composition according to claim 1, wherein, a mass ratio of the component (A) to the component (B), (A)/(B), is from 0.1 to 10.

6. The cosmetic composition according to claim 1, wherein, a mass ratio of the component (A) to the component (D), (A)/(D), is from 4 to 15.

7. The cosmetic composition according to claim 1, wherein, in the formulae (1) and (2) of the component (A), m is from 2 to 5; n is from 1 to 4; p is from 3 to 10; and s is from 1 to 3.

8. The cosmetic composition according to claim 1, wherein, in the formulae (1) and (2) of the component (A), a ratio of p/(p+s) satisfies 0.75≤p/(p+s)≤0.83.

9. The cosmetic composition according to claim 1, wherein, the component (B) has an average particle diameter of from 0.1 to 20 μm.

10. The cosmetic composition according to claim 1, wherein, the component (C) is a fine zinc oxide particle having been subjected to a silicone treatment.

11. The cosmetic composition according to claim 1, wherein, the organopolysiloxane of the component (D) is produced by reacting a modified organopolysiloxane with a terminal reactive poly(N-acylalkyleneimine), the modified organopolysiloxane being represented by the following formula (6):

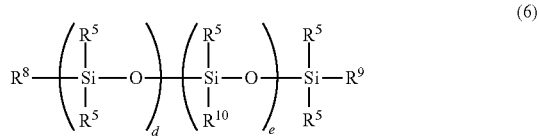

wherein, $R^5$ each independently represent an alkyl group having 1 to 22 carbon atoms or a phenyl group; and $R^8$ and $R^9$ each represent the same group as $R^5$ or a monovalent group represented by any of the following formulae (viii) to (xiii):

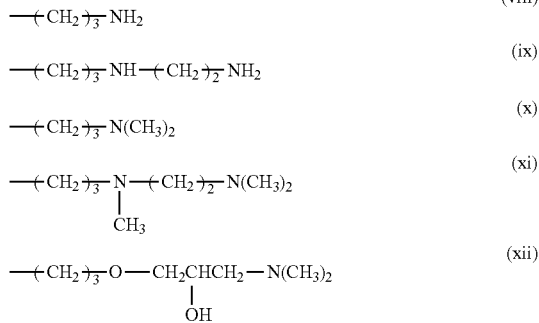

$R^{10}$ represents a monovalent group represented by the above formulae (viii) to (xiii); d represents a number of from 91.5 to 1255.0; and e represents a number of from 2.0 to 62.5, and the terminal reactive poly(N-acylalkyleneimine) being obtainable by ring-opening polymerization of a cyclic imino ether represented by the following formula (7):

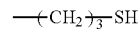

wherein, $R^4$ and t have the same meaning as above, and wherein, a mass ratio of the modified organopolysiloxane represented by the formula (6) to the terminal reactive poly(N-acylalkyleneimine), (modified organopolysiloxane/terminal reactive poly(N-acylalkyleneimine)), is from 83/17 to 93/7.

12. The cosmetic composition according to claim 11, wherein, a mass ratio of the modified organopolysiloxane represented by the formula (6) to the terminal reactive poly (N-acylalkyleneimine), (modified organopolysiloxane/terminal reactive poly(N-acylalkyleneimine)), is from 85/15 to 90/10.

13. The cosmetic composition according to claim 1, wherein, a water content is from 10 to 60% by mass.

14. The cosmetic composition according to claim 1, further comprising an oil agent which is liquid at 20° C., which is at least one selected from the group consisting of a silicone oil, a hydrocarbon oil and an ester oil, wherein a content thereof is from 10 to 50% by mass.

15. The cosmetic composition according to claim 1, further comprising a surfactant, wherein the surfactant is a nonionic surfactant.

16. The cosmetic composition according to claim 15, wherein the surfactant is a polyether-modified silicone.

17. The cosmetic composition according to claim 15, wherein, the nonionic surfactant has an HLB value of 1 or more and 7 or less.

18. The cosmetic composition according to claim 15, wherein, a content of the surfactant is from 0.1 to 6% by mass.

19. The cosmetic composition according to claim 1, wherein, the cosmetic composition is a water-in-oil type emulsified cosmetic composition.

20. The cosmetic composition according to claim 1, which is a liquid foundation, a makeup base, a sunscreen emulsion, or a sunscreen cream.

21. A method for using the cosmetic composition according to claim 1, comprising applying the composition to the skin using a sponge.

* * * * *